(12) United States Patent
Denham et al.

(10) Patent No.: US 8,986,345 B2
(45) Date of Patent: Mar. 24, 2015

(54) EXPANDING SUTURE ANCHOR HAVING AN ACTUATOR PIN

(75) Inventors: Gregory J. Denham, Warsaw, IN (US); Kevin T. Stone, Winona Lake, IN (US); Ryan A. Kaiser, Leesburg, IN (US); Jason D. Meridew, Warsaw, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 1810 days.

(21) Appl. No.: 11/451,250

(22) Filed: Jun. 12, 2006

(65) Prior Publication Data

US 2006/0235413 A1     Oct. 19, 2006

Related U.S. Application Data

(63) Continuation-in-part of application No. 11/006,398, filed on Dec. 7, 2004, now Pat. No. 7,976,565.

(51) Int. Cl.
*A61B 17/04* (2006.01)

(52) U.S. Cl.
CPC ..... *A61B 17/0401* (2013.01); *A61B 2017/0408* (2013.01); *A61B 2017/0409* (2013.01); *A61B 2017/0414* (2013.01); *A61B 2017/0458* (2013.01)
USPC ........................................................ 606/232

(58) Field of Classification Search
CPC ........... A61B 17/0401; A61B 17/0487; A61B 2017/0412; A61B 2017/0437
USPC ................................................ 606/228, 232
See application file for complete search history.

(56) References Cited

U.S. PATENT DOCUMENTS

| | | | |
|---|---|---|---|
| 3,708,883 | A | 1/1973 | Flander |
| 4,409,974 | A | 10/1983 | Freedland |
| 4,653,489 | A | 3/1987 | Tronzo |
| 4,738,255 | A | 4/1988 | Goble et al. |
| 5,013,316 | A | 5/1991 | Goble et al. |
| 5,087,199 | A | 2/1992 | Lazarof |
| 5,167,665 | A | 12/1992 | McKinney |
| 5,258,016 | A | 11/1993 | DiPoto et al. |
| 5,268,001 | A | 12/1993 | Nicholson et al. |
| 5,326,205 | A | 7/1994 | Anspach, Jr. et al. |
| 5,464,427 | A | 11/1995 | Curtis et al. |
| 5,472,452 | A | 12/1995 | Trott |
| 5,474,572 | A * | 12/1995 | Hayhurst ................. 606/232 |
| 5,480,403 | A | 1/1996 | Lee et al. |
| 5,486,197 | A | 1/1996 | Le et al. |
| 5,501,695 | A | 3/1996 | Anspach, Jr. et al. |
| 5,531,792 | A | 7/1996 | Huene |
| 5,584,835 | A | 12/1996 | Greenfield |
| 5,601,558 | A | 2/1997 | Torrie et al. |
| 5,643,321 | A * | 7/1997 | McDevitt ................. 606/232 |
| 5,645,589 | A | 7/1997 | Li |
| 5,649,963 | A | 7/1997 | McDevitt |
| 5,665,110 | A | 9/1997 | Chervitz et al. |
| 5,713,903 | A | 2/1998 | Sander et al. |

(Continued)

*Primary Examiner* — Gregory Anderson
*Assistant Examiner* — Christina Lauer
(74) *Attorney, Agent, or Firm* — Harness, Dickey

(57) ABSTRACT

A method and apparatus for reattaching soft tissue to a boney structure using an expanding suture anchor. The method can include providing a suture anchor and forming a cavity in the boney structure for receipt of the suture anchor. The method can also include coupling the soft tissue to a suture and coupling the suture to the suture anchor. The method can further include deploying the suture anchor to fix the suture to the suture anchor and the suture anchor to the cavity.

24 Claims, 31 Drawing Sheets

(56) References Cited

U.S. PATENT DOCUMENTS

| | | | |
|---|---|---|---|
| 5,720,753 A | 2/1998 | Sander et al. | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,772,672 A * | 6/1998 | Toy et al. | 606/139 |
| 5,814,071 A | 9/1998 | McDevitt et al. | |
| 5,911,721 A | 6/1999 | Nicholson et al. | |
| 5,928,244 A | 7/1999 | Tovey et al. | |
| 5,931,844 A | 8/1999 | Thompson et al. | |
| 5,935,129 A | 8/1999 | McDevitt et al. | |
| 5,941,901 A | 8/1999 | Egan | |
| 5,948,000 A * | 9/1999 | Larsen et al. | 606/232 |
| 5,968,044 A | 10/1999 | Nicholson et al. | |
| 6,022,373 A * | 2/2000 | Li | 606/232 |
| 6,048,343 A | 4/2000 | Mathis et al. | |
| 6,056,751 A | 5/2000 | Fenton, Jr. | |
| 6,129,762 A | 10/2000 | Li | |
| 6,149,669 A | 11/2000 | Li | |
| 6,210,376 B1 | 4/2001 | Grayson | |
| 6,214,012 B1 | 4/2001 | Karpman et al. | |
| 6,227,860 B1 | 5/2001 | Hobo et al. | |
| 6,315,787 B1 | 11/2001 | Tsugita et al. | |
| 6,319,269 B1 | 11/2001 | Li | |
| 6,328,758 B1 | 12/2001 | Tornier et al. | |
| 6,447,516 B1 | 9/2002 | Bonutti | |
| 6,464,706 B1 | 10/2002 | Winters | |
| 6,517,564 B1 | 2/2003 | Grafton et al. | |
| 6,524,316 B1 | 2/2003 | Nicholson et al. | |
| 6,527,794 B1 | 3/2003 | McDevitt et al. | |
| 6,554,830 B1 | 4/2003 | Chappius | |
| 6,565,572 B2 | 5/2003 | Chappius | |
| 6,575,976 B2 | 6/2003 | Grafton | |
| 6,582,453 B1 | 6/2003 | Tran et al. | |
| 6,599,295 B1 | 7/2003 | Tornier et al. | |
| 6,623,492 B1 | 9/2003 | Berube et al. | |
| 6,641,596 B1 | 11/2003 | Lizardi | |
| 6,645,227 B2 | 11/2003 | Fallin et al. | |
| 6,652,561 B1 | 11/2003 | Tran | |
| 6,660,023 B2 | 12/2003 | McDevitt et al. | |
| 6,770,073 B2 | 8/2004 | McDevitt et al. | |
| 6,863,671 B1 | 3/2005 | Strobel et al. | |
| 6,994,725 B1 | 2/2006 | Goble | |
| 7,037,324 B2 | 5/2006 | Martinek | |
| 7,250,055 B1 | 7/2007 | Vanderwalle | |
| 7,572,283 B1 | 8/2009 | Meridew | |
| 2001/0051807 A1 | 12/2001 | Grafton | |
| 2002/0013608 A1 * | 1/2002 | ElAttrache et al. | 606/232 |
| 2002/0095180 A1 * | 7/2002 | West et al. | 606/228 |
| 2002/0111653 A1 | 8/2002 | Foerster | |
| 2002/0128684 A1 | 9/2002 | Foerster | |
| 2002/0147463 A1 * | 10/2002 | Martinek | 606/232 |
| 2002/0188321 A1 * | 12/2002 | Levinson | 606/232 |
| 2003/0144667 A1 | 7/2003 | Enayati | |
| 2003/0187444 A1 | 10/2003 | Overaker et al. | |
| 2004/0133239 A1 * | 7/2004 | Singhatat | 606/232 |
| 2004/0138707 A1 * | 7/2004 | Greenhalgh | 606/232 |
| 2004/0193167 A1 | 9/2004 | Tucciarone et al. | |
| 2004/0225292 A1 | 11/2004 | Sasso et al. | |
| 2004/0243179 A1 | 12/2004 | Foerster | |
| 2004/0267265 A1 | 12/2004 | Kyle | |
| 2005/0015059 A1 | 1/2005 | Sweeney | |
| 2005/0075668 A1 | 4/2005 | Lizardi | |
| 2005/0137707 A1 | 6/2005 | Malek | |
| 2006/0004364 A1 * | 1/2006 | Green et al. | 606/72 |
| 2007/0112352 A1 * | 5/2007 | Sorensen et al. | 606/73 |
| 2007/0265704 A1 | 11/2007 | Mayer et al. | |
| 2008/0281325 A1 | 11/2008 | Stone et al. | |
| 2009/0299386 A1 | 12/2009 | Meridew | |
| 2011/0004258 A1 | 1/2011 | Stone et al. | |

\* cited by examiner

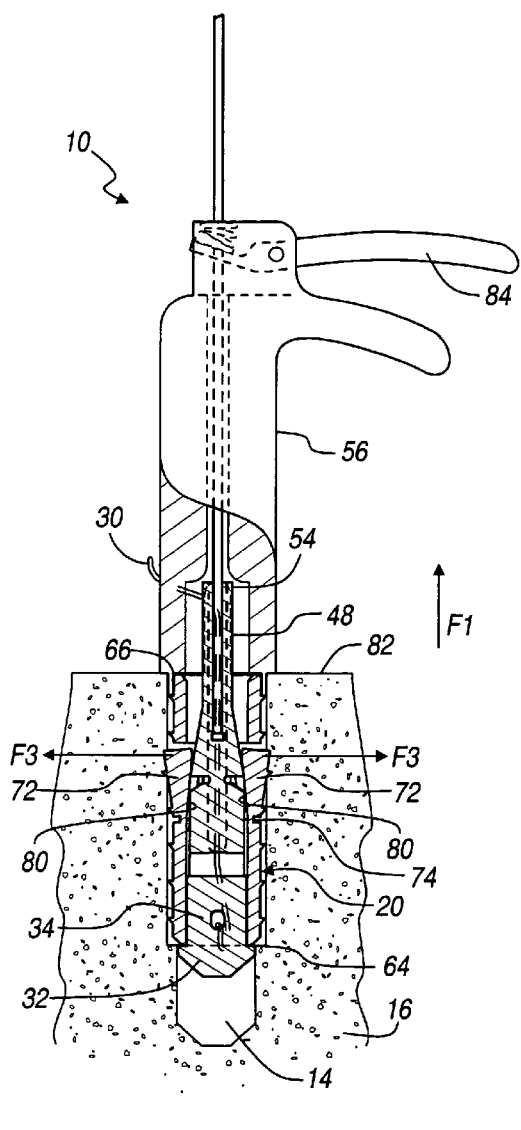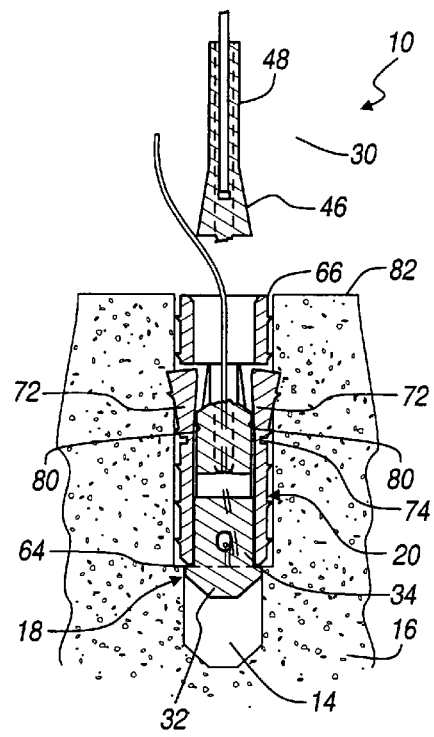
FIG. 4B
FIG. 4C

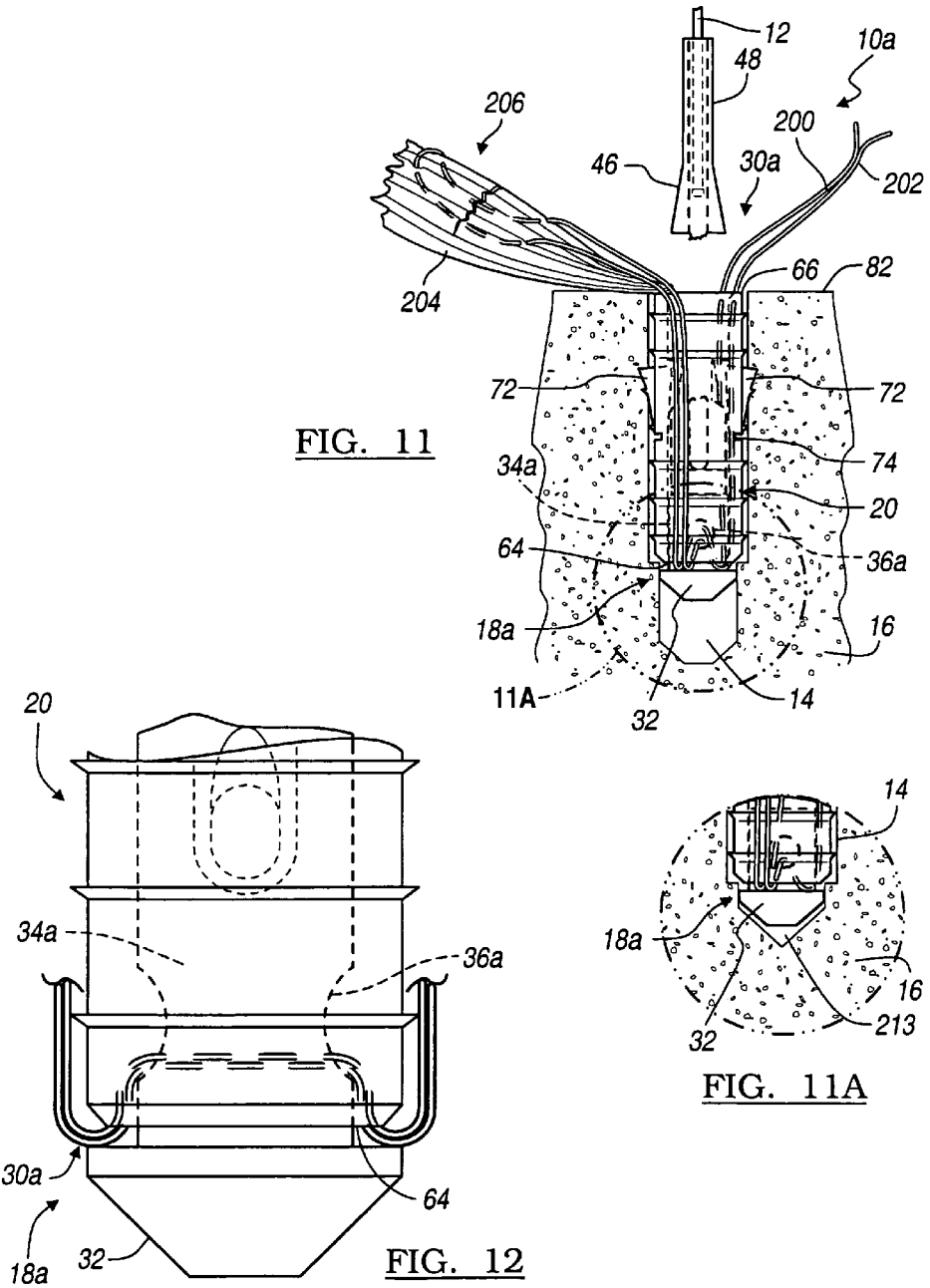

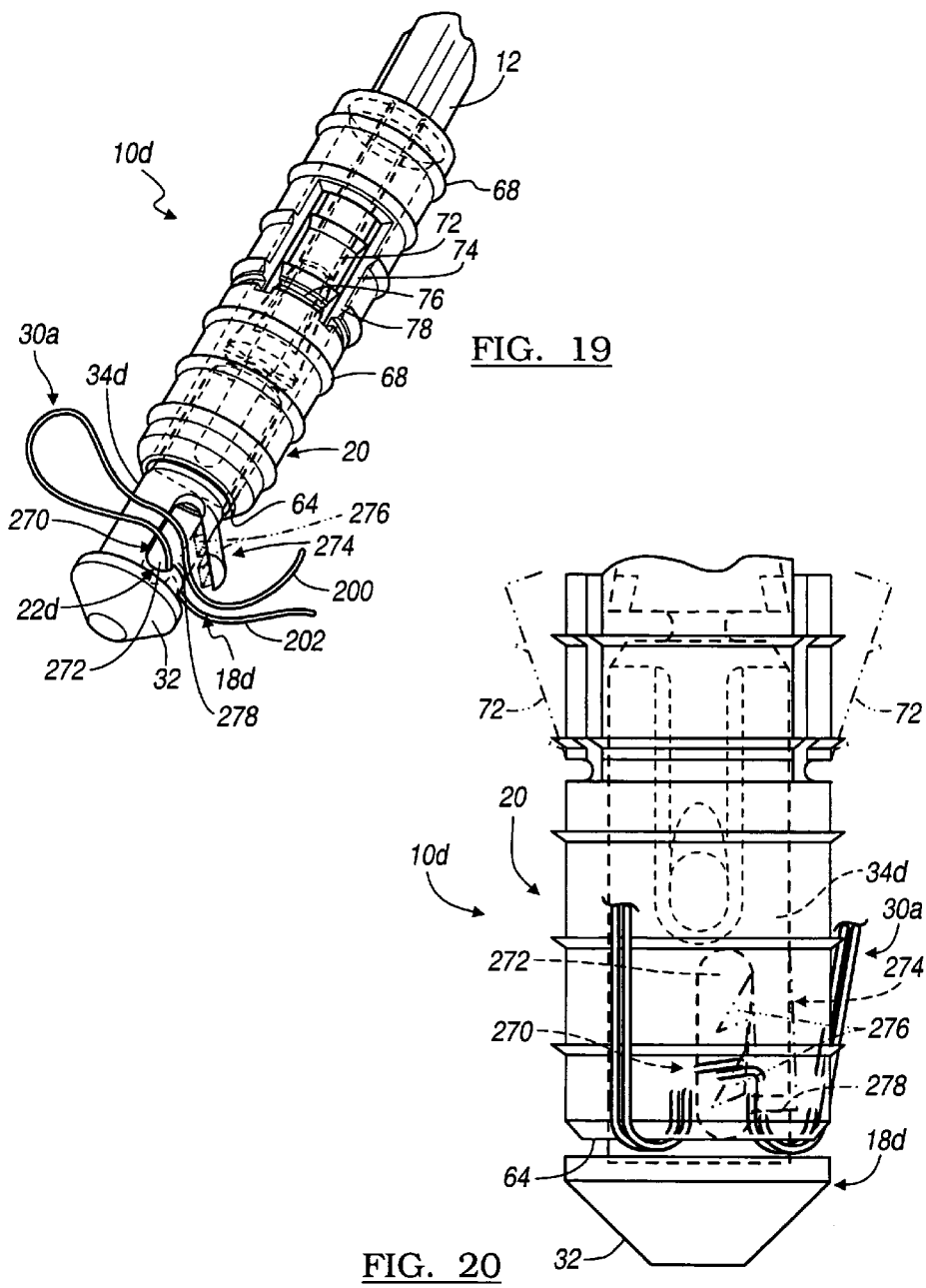

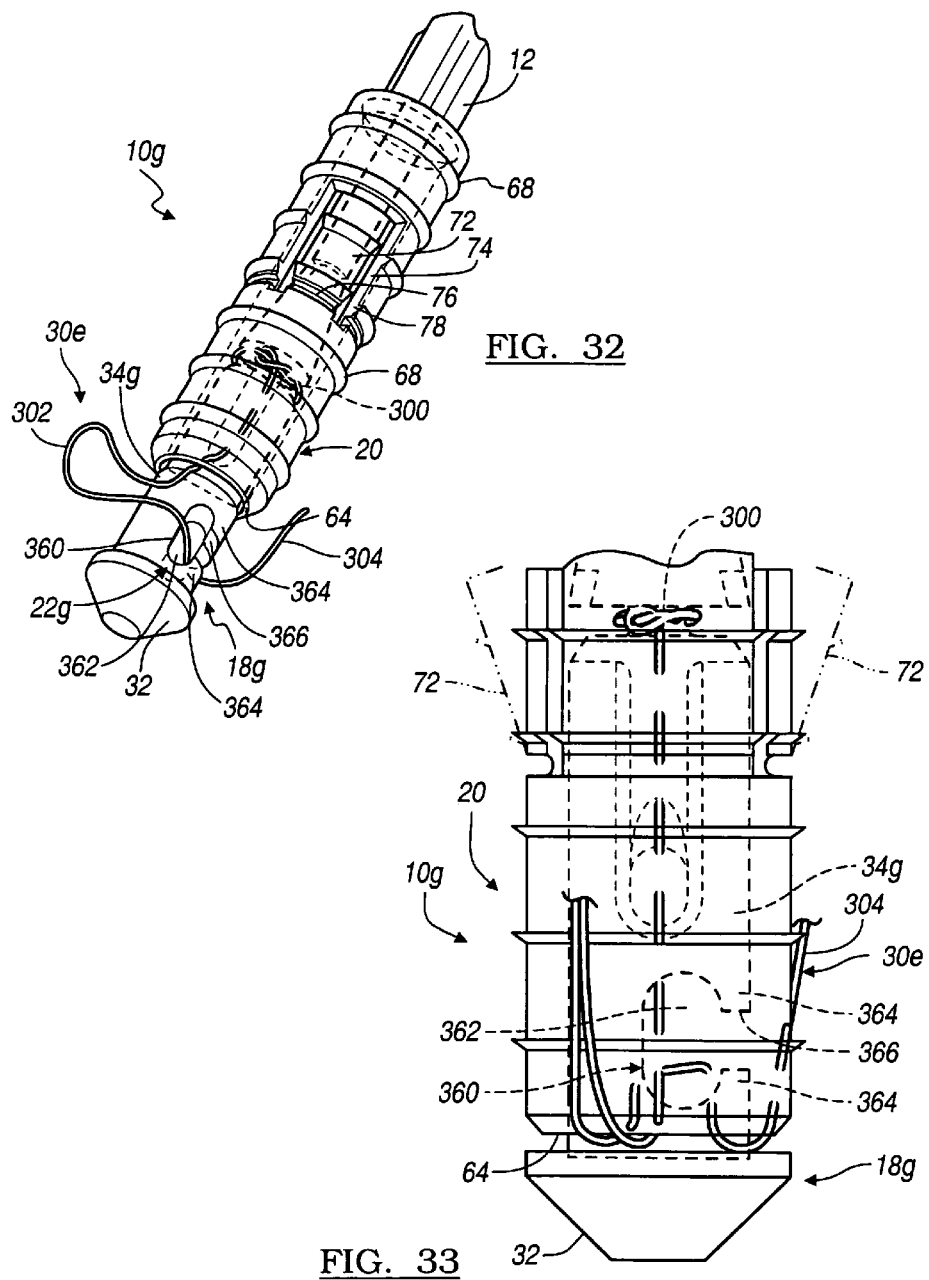

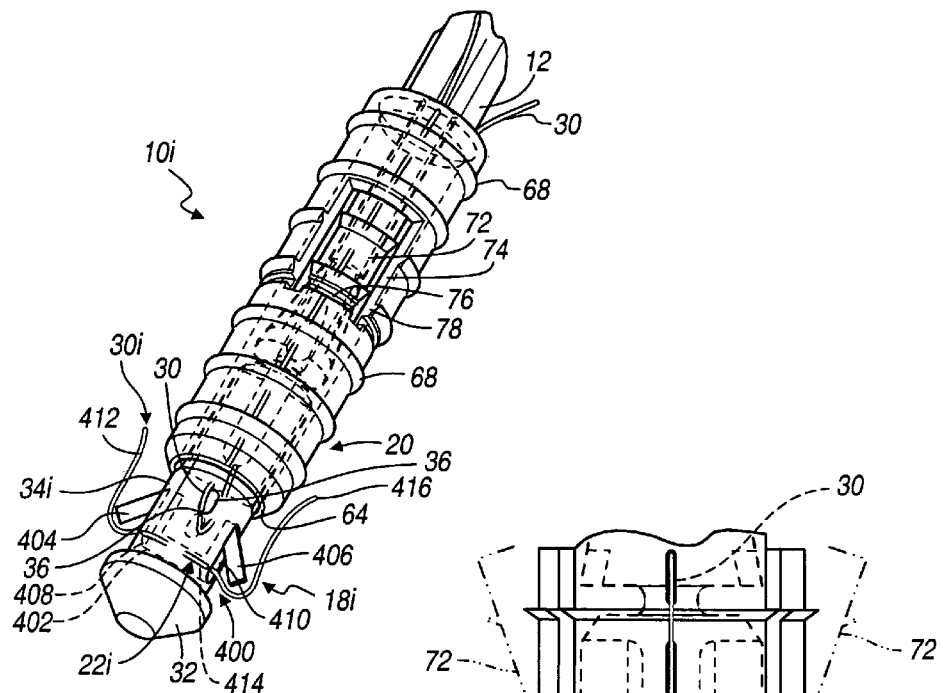
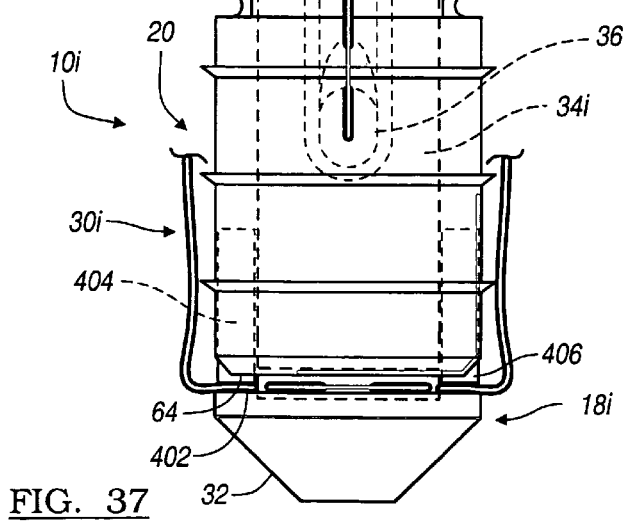
FIG. 36
FIG. 37

EXPANDING SUTURE ANCHOR HAVING AN ACTUATOR PIN

CROSS-REFERENCE TO RELATED APPLICATIONS

This application is a continuation-in-part of U.S. patent application Ser. No. 11/006,398 filed on Dec. 7, 2005. The disclosure of the above application is incorporated herein by reference.

FIELD

The present disclosure relates generally to suture anchors, and particularly to a method and apparatus for an expanding suture anchor having an actuator pin.

BACKGROUND

The statements in this section merely provide background information related to the present disclosure and may not constitute prior art.

Various procedures may be performed to repair soft tissue in the body. Generally, it is known to fix the soft tissue to a selected area on the bone by providing a suture through a selected portion of the soft tissue while securing the other end of the suture to the selected area on the bone using a suture anchor.

Suture anchors may be retained in the selected area of the bone via a feature of the suture anchor. In hard bone, however, the suture anchor may not fully engage the bone because the surgeon is not able to apply sufficient force to the suture. Thus, the suture may become loose in the boney structure, which could lead to increased healing times or improper healing. In addition, some of the techniques used to lock the suture to the suture anchor can be labor intensive. Therefore, it may be desirable to provide a method and apparatus for an expanding suture anchor, and a method and apparatus for locking a suture to such a suture anchor.

SUMMARY

A method for attaching a soft tissue to a boney structure. The method can include providing a suture anchor and forming a cavity in the boney structure for receipt of the suture anchor. The method can also include coupling the soft tissue to a suture and coupling the suture to the suture anchor. The method can further include deploying the suture anchor to fix the suture to the suture anchor and the suture anchor to the cavity.

Also provided is a method for attaching a soft tissue to a boney structure. The method can include providing a suture anchor defining an aperture and forming a cavity in the boney structure for receipt of the suture anchor. The method can further include coupling the soft tissue to a suture and threading at least one end of the suture through the aperture of the suture anchor. The method can include disposing the suture anchor in the cavity and deploying the suture anchor to fix the suture anchor to the cavity. The deployment of the suture anchor can fix the suture to the suture anchor without the use of a knot.

A method for attaching a soft tissue to a boney structure is also provided. The method can include providing a suture anchor and forming a cavity in the boney structure for receipt of the suture anchor. The method can also include coupling the soft tissue to a suture and coupling the suture to the suture anchor. The method can also include disposing the suture anchor in the cavity and applying a retractive force to the suture anchor. The retractive force can fix the suture in the suture anchor.

A suture anchor for attaching soft tissue to a pre-selected area of a boney structure is further provided. The suture anchor can include an expanding anchor for engaging the boney structure and an insert slideably coupled to the expanding anchor. The insert can be moveable to cause the expanding anchor to expand and engage the boney structure. An aperture can be defined in the insert, and a suture can be received in the aperture. The suture can be adapted to be coupled to the soft tissue. The movement of the insert can fix the suture to the expanding anchor.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4B is an environmental view of the suture anchor as the retractive force is applied to move the suture anchor into the fully expanded position;

FIG. 4C is an environmental view illustrating the suture anchor in a fully expanded position;

FIG. 11 is an environmental view illustrating the suture anchor of FIG. 7 in a fully expanded position;

FIG. 11A is an alternative environmental partial view illustrating the suture anchor of FIG. 7 in a fully expanded position;

FIG. 12 is detailed front view of the suture anchor of FIG. 7 illustrating a suture fixed to the suture anchor;

FIG. 19 is a perspective view of a fourth alternative expanding suture anchor having an actuator pin according to the present disclosure;

FIG. 20 is detailed front view of the suture anchor of FIG. 19 illustrating a suture fixed to the suture anchor;

FIG. 32 is a perspective view of a seventh alternative expanding suture anchor having an actuator pin according to the present disclosure;

FIG. 33 is detailed front view of the suture anchor of FIG. 32 illustrating a suture fixed to the suture anchor;

DETAILED DESCRIPTION

The following description of various embodiments is merely exemplary in nature and is in no way intended to limit the present teachings, their application, or uses. Although the following description is related generally to a suture anchor that can be positioned in a pre-drilled hole, that is a hole provided in a boney structure for acceptance of the suture anchor, it will be understood that a suture anchor including an impacting tip or self-drilling thread may be provided as well. Moreover, it will be understood that the suture anchor, as described and claimed herein, can be used with any appropriate surgical procedure. Therefore, it will be understood that the following discussions is not intended to limit the scope of the appended claims.

Figure 1:
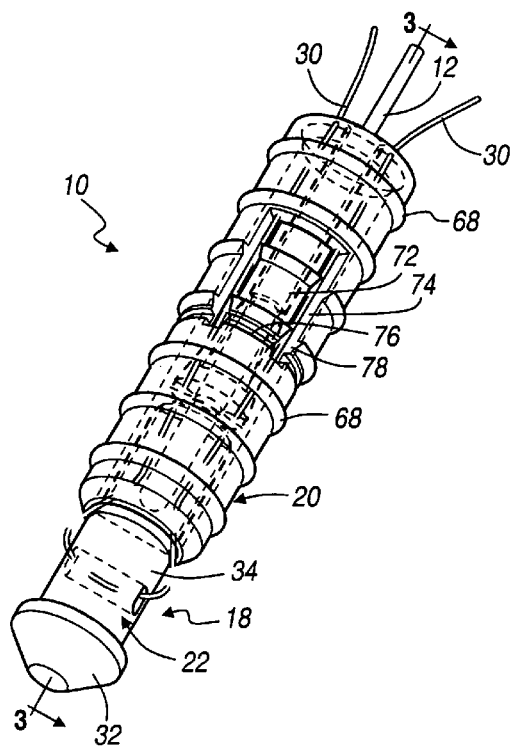
FIG. 1 is a perspective view of an expanding suture anchor having an actuator pin according to the present disclosure.
Figure 4A:
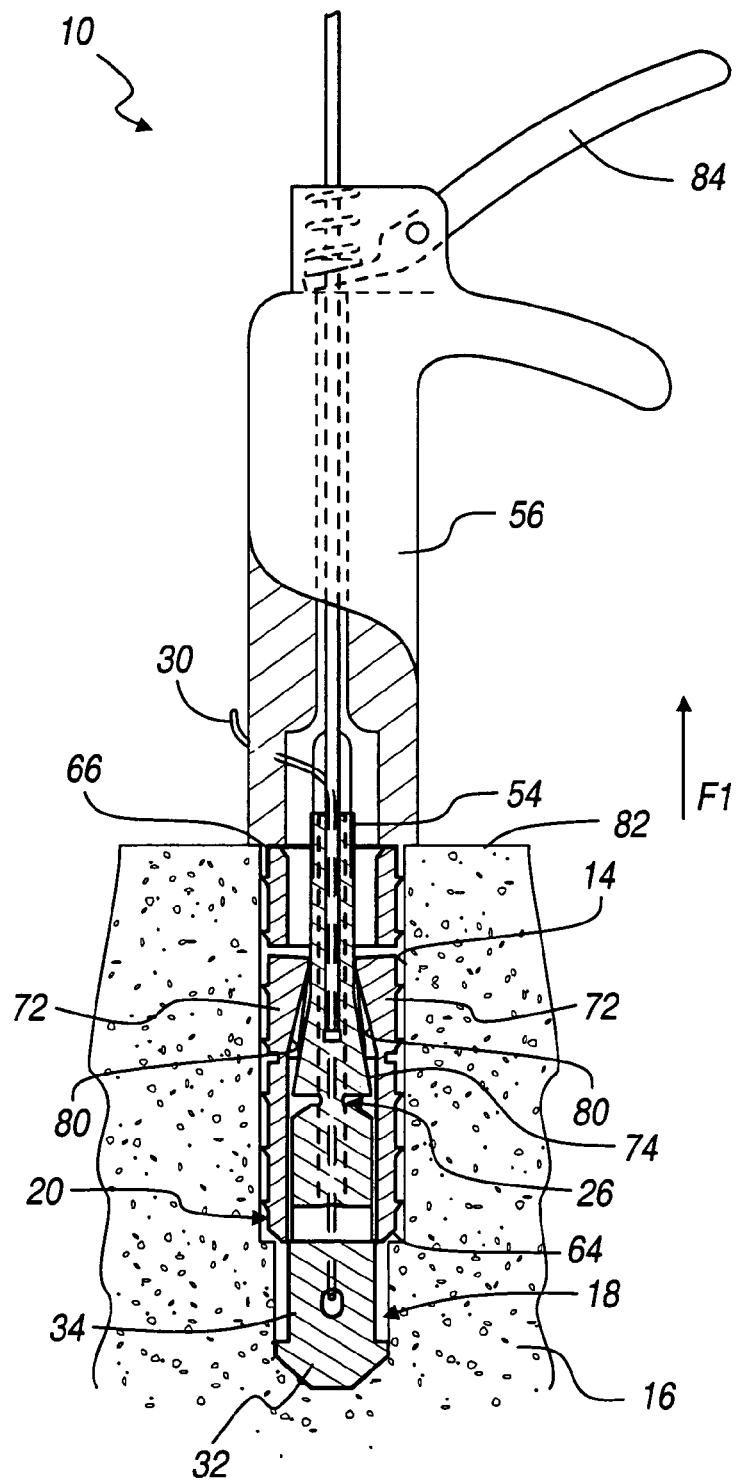
FIG. 4A is an environmental view of a use of the suture anchor shown in FIG. 1.

With reference to FIG. 1, an expanding suture anchor 10 having an actuator pin 12 is illustrated. The suture anchor 10 is operable in a first configuration for insertion into a pre-drilled hole 14 in a boney structure 16 (as shown in FIG. 4A) and operable in a second configuration to secure the suture anchor 10 in the pre-drilled hole 14 (as shown in FIG. 4C). The suture anchor 10 generally includes an insert 18 molded to the actuator pin 12 and partially disposed in a sleeve 20.

Figure 3A:
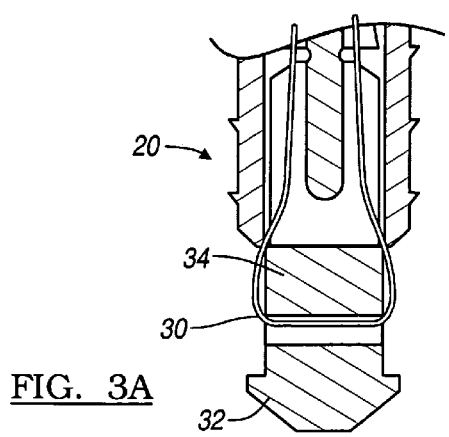
FIG. 3A is a detailed view of FIG. 3.
Figure 3:
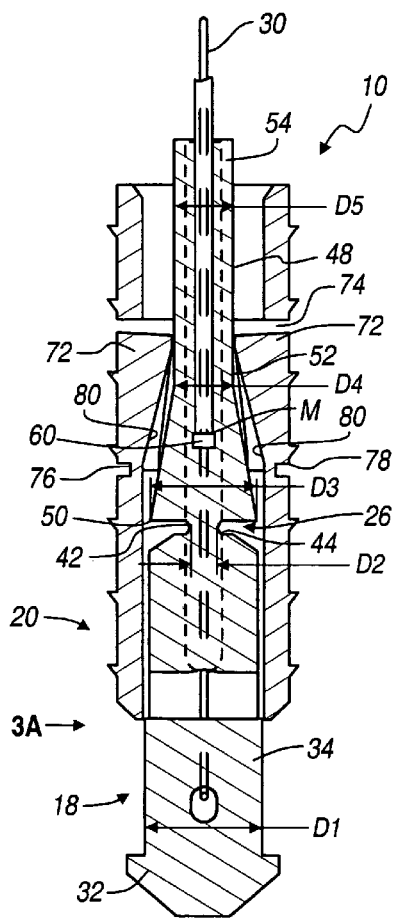
FIG. 3 is a cross-sectional view taken along line 3-3 of FIG. 1.
Figure 2:
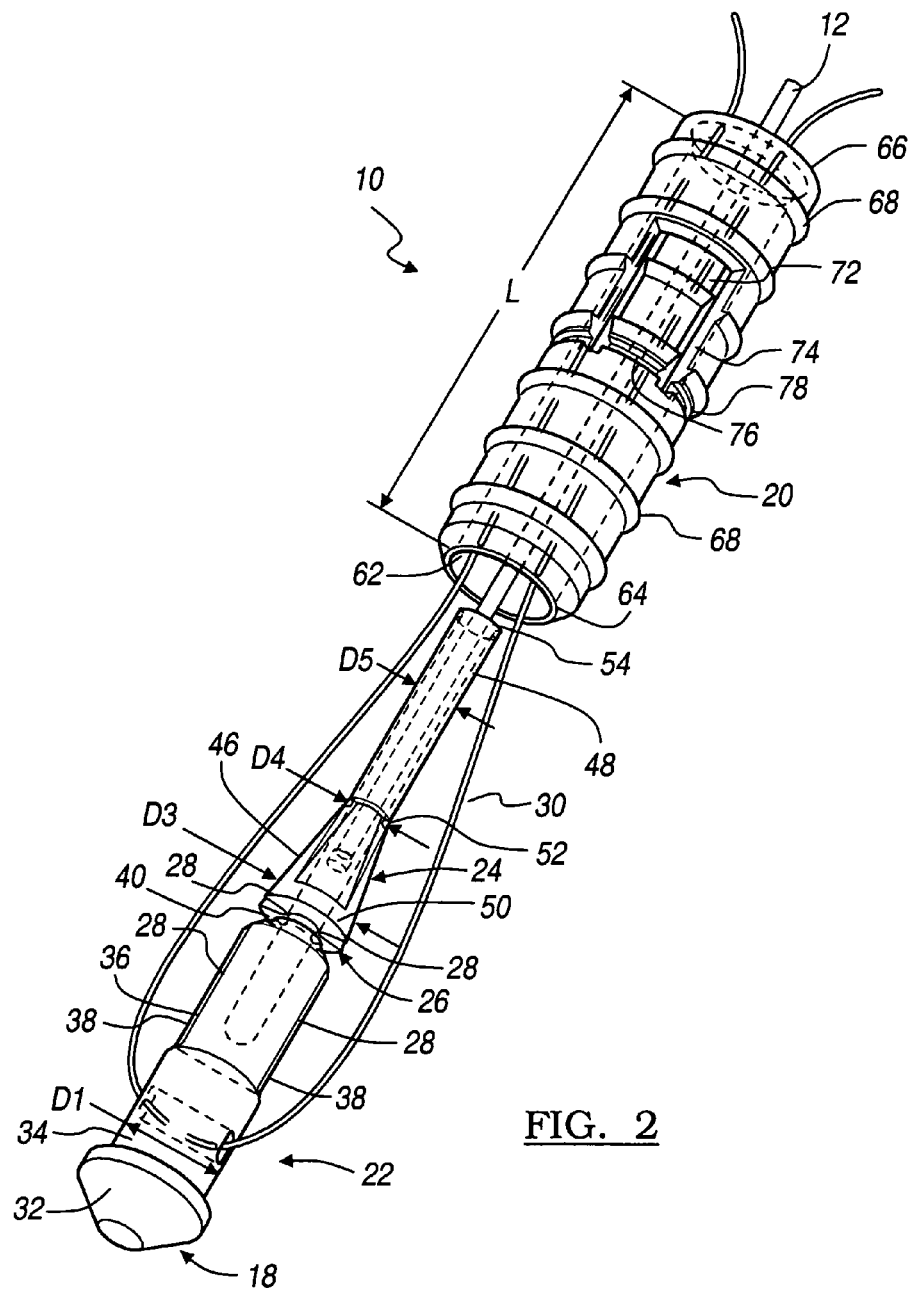
FIG. 2 is an exploded view of the suture anchor in FIG. 1.

With continuing reference to FIG. 1 and additional reference to FIGS. 2 and 3, the insert 18 includes a suture receiving portion 22 and an end section 24 displaced from the suture receiving portion 22 by a breakaway section 26. The suture receiving portion 22 and end section 24 have a tensile and a torsion strength that are greater than the tensile and torsion strength of the breakaway section 26 such that the suture receiving portion 22 and end section 24 will be severed by the breakaway section 26 without damage to the structural integrity of either section. The insert 18 is generally insert molded from a resorbable material (such as, for example, Lactosorb®, available from Biomet Inc. of Warsaw, Ind.); however, it will be understood that other types of biocompatible materials and other methods of forming could be used.

At least one groove 28 extends throughout a length L1 of the suture receiving portion 22 and the end section 24 for receipt of strands from a suture 30 therein. The suture receiving portion 22 further has a tip 32 and a cylindrical body 34. The tip 32 is generally conical in shape; however, any other desired shape may be used. The cylindrical body 34 has a diameter D1, which is sized to ensure a slip fit with the sleeve 20 such that the cylindrical body 34 can slide within the sleeve 20. The cylindrical body 34 includes a formed eyelet 36 extending through the cylindrical body 34 to provide an attachment point for the suture 30, as shown in FIG. 3A. The diameter D1 of the cylindrical body can provide an interference fit with regard to the suture 30 fitting between the cylindrical body 34 and the sleeve 20. Referring back to FIG. 3, the cylindrical body 34 may further include a tapered section 40 leading to the breakaway section 26.

The breakaway section 26 has a diameter D2, which is generally one-half the size of the diameter D1 of the cylindrical body 34. The breakaway section 26 may include two necked portions 42, 44, which facilitate the fracturing of the breakaway section 26 by reducing the fracture strength of the breakaway section 26 in torsion and tension as compared to the suture receiving portion 22 and the end section 24. The diameter of the necked portions 42, 44 may vary to enable different fracture loads for various applications; however, generally the force required to fracture the necked portions 42, 44 will be between 10-12 foot-pounds. The fracturing of the breakaway section 26 detaches the suture receiving portion 22 from the end section 24 of the insert 18 (as illustrated in FIG. 4C).

With continued reference to FIG. 3 and additional reference to FIG. 2, the end section 24 has a tapered portion 46 coupled to an annular body 48. The tapered portion 46 includes a first diameter D3 at a first end 50, which tapers to a second diameter D4 at a second end 52. In general, the first diameter D3 of the tapered portion 46 is approximately equal to the diameter D1 of the suture receiving portion 22. The tapered portion 46 operates to place the suture anchor 10 in the second position to engage the boney structure 16 as will be described in greater detail below. The second end 52 of the tapered portion 46 is coupled to the annular body 48. The annular body 48 is generally cylindrical and has a constant diameter D5. The diameter D5 of the annular body 48 may be larger than or equal to the second diameter D4 of the tapered portion 46, yet smaller than the first diameter D3 of the tapered portion 46. The annular body 48 can extend beyond the sleeve 20 when the suture anchor 10 is assembled to provide a locator 54 for an actuator gun 56 (as shown in FIG. 4A) for the application of a retractive force F1; however, this is not necessary, as will be discussed further below. The annular body 48 and tapered portion 46 each further include a formed central bore 58 for receipt of the actuator pin 12 therein.

The actuator pin 12 is fixedly attached to the annular body 48 and tapered portion 46 via insert molding. In particular, the insert 18 is formed around the actuator pin 12, ensuring secure and precise attachment. The actuator pin 12 is positioned in the formed central bore 58 of the annular body 48 and tapered portion 46 such that the actuator pin 12 is removed from the suture anchor 10 when the breakaway section 26 is fractured. The actuator pin 12 can be made of any suitable biocompatible corrosive resistance material such as, for example, surgical steel. In this regard, the actuator pin 12 need not be made of the same material as the sleeve 20.

The actuator pin 12 further includes a formed cavity 60 that retains the actuator pin 12 in the insert 18 through out the application of the retractive force F1. More specifically, as best shown in FIG. 3, as the insert 18 is formed around the actuator pin 12, material M is formed under the cavity 60. Thus, this material M must be displaced in order to remove the actuator pin 12 from the insert 18. Accordingly, the retractive force F1 must be less than the fracture strength of the material M to ensure the actuator pin 12 is retained in the insert 18. Similarly, the size of the cavity 60 can be modified to allow the accumulation of varying amounts of material M depending on the amount of retractive force F1 required to secure the suture anchor 10 in a given boney structure.

With continuing reference to FIGS. 2 and 3 and additional reference to FIG. 1, the sleeve 20 is disposed about a substantial portion of the insert 18. More specifically, the sleeve 20 includes a throughbore 62 for receipt of the insert 18 therein. The sleeve 20 has a length L, which may be configured such that the suture receiving portion 22 and locator 54 are exposed when the suture anchor 10 is in the first position. For example, a first end 64 of sleeve 20 is shown covering the breakaway section 26 and approximately one half of the cylindrical body 34 of the suture receiving portion 22 and a second end 66 of the sleeve 20 covers the tapered portion 46 and approximately one half of the annular body 48 of the end section 24. The sleeve 20 is typically made from a resorbable material (such as, for example, Lactosorb®, available from Biomet Inc. of Warsaw, Ind.); however, other suitable materials could be employed.

The sleeve 20 is generally cylindrical in nature, and may include at least one ring or securement device 68 on an external surface 70 of the sleeve 20. Although the sleeve 20 is shown having a ring 68, it is to be understood various other external features could be disposed on the sleeve 20 (such as, for example, barbs or threads). The at least one ring 68 further aids in the engagement of the suture anchor 10 in the pre-drilled hole 14. The sleeve 20 also includes at least one expanding member 72 hingably coupled to the sleeve 20 to engage the pre-drilled hole 14. Specifically, the expanding member 72 is defined by a slot 74 formed in the sleeve 20 and includes a hinge 76. In one embodiment, the sleeve 20 includes two expanding members 72 located approximately 180 degrees apart. It shall be noted, however, that the expanding members 72 could be located at any position on the sleeve 20 that would engage the boney structure 16. The expanding members 72 are located at a midsection 78 of the sleeve 20. The expanding members 72 expand to lock into the boney structure 16 when the retractive force F1 is applied to the actuator pin 12 and, in turn, to a tapered interior bearing surface 80 on the expanding members 72.

With reference now to FIG. 4A, after the pre-drilled hole 14 has been drilled into the boney structure 16 and the eyelet 36 of the insert 18 has been threaded with the suture 30, the suture anchor 10 can be inserted into the pre-drilled hole 14 as shown. The suture anchor 10 is generally configured such that only the locator 54 of the end section 24 extends beyond a top surface 82 of the boney structure 16.

Figure 4D:
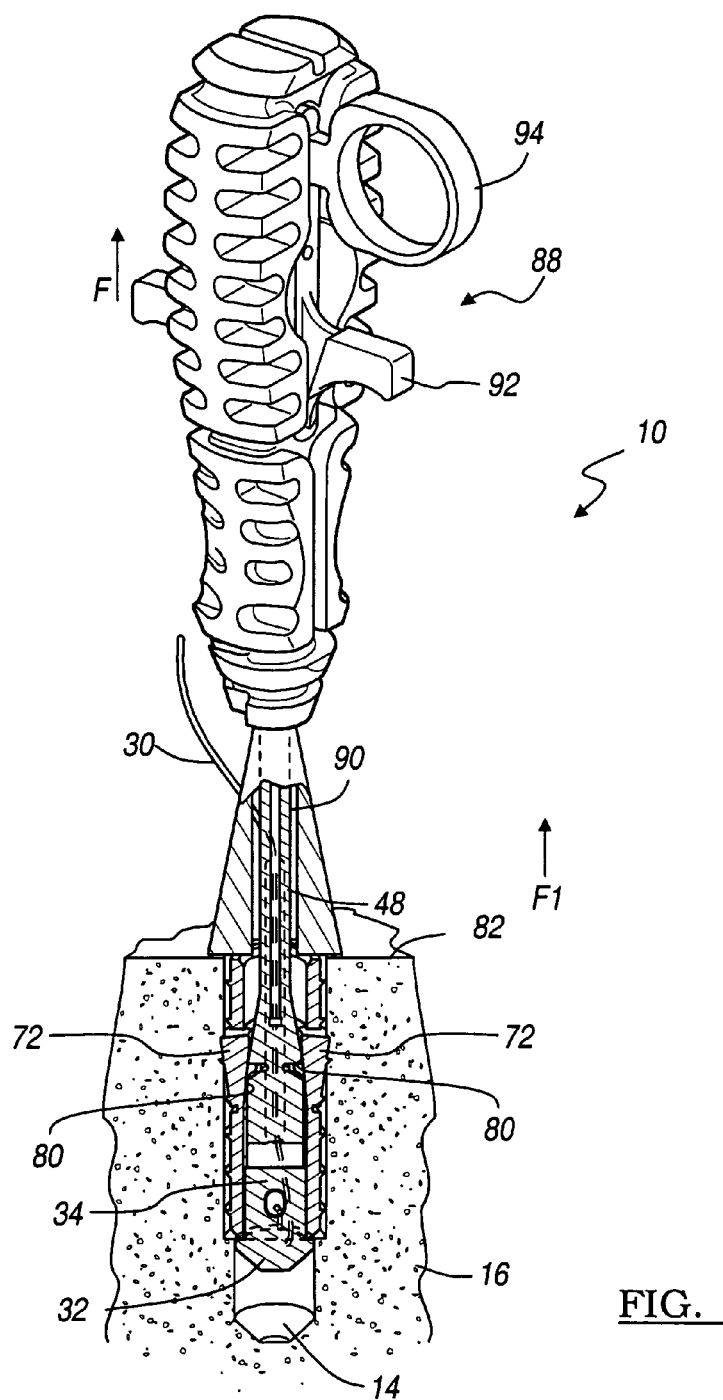
FIG. 4D is an environmental view illustrating an alternate actuator gun for use with the suture anchor shown in FIG. 1.

Next, the actuator gun 56 is applied to the suture anchor 10 as shown in FIGS. 4A and 4B. When a trigger 84 on the actuator gun 56 is pulled, the actuator gun 56 applies the retractive force F1 to the actuator pin 12. It should be noted, however, that the actuator gun 56 may not be the only actuating device capable of applying the retractive force F1 to the suture anchor 10. In particular, numerous other devices may be employed (such as, for example, a syringe-type actuator 88, as shown in FIG. 4D). In FIG. 4D, the syringe-type actuator 88 includes a cannula 90 that engages the actuator pin 12. A lever 92 can be used to retract the cannula 90 by the application of a force F to the lever 92. More specifically, the lever 92 operates to retract the cannula 90 once it is engaged with the actuator pin 12 to provide the retractive force F1 to the suture anchor 10. A stop 94 can also be provided to prevent the lever 92 from prematurely applying the retractive force F1.

The application of the retractive force F1 causes the insert 18 to displace rearwardly with respect to the sleeve 20, as illustrated in FIG. 4B. This rearward displacement causes the tapered portion 46 to apply a force F3 to the tapered interior bearing surface 80 of the expanding members 72 of the sleeve 20. As the insert 18 continues to move rearward, the tapered portion 46 applies an increasingly greater force F3 to the tapered interior bearing surface 80 of the expanding members 72 until the expanding members 72 are engaged with the boney structure 16.

Figure 5A:
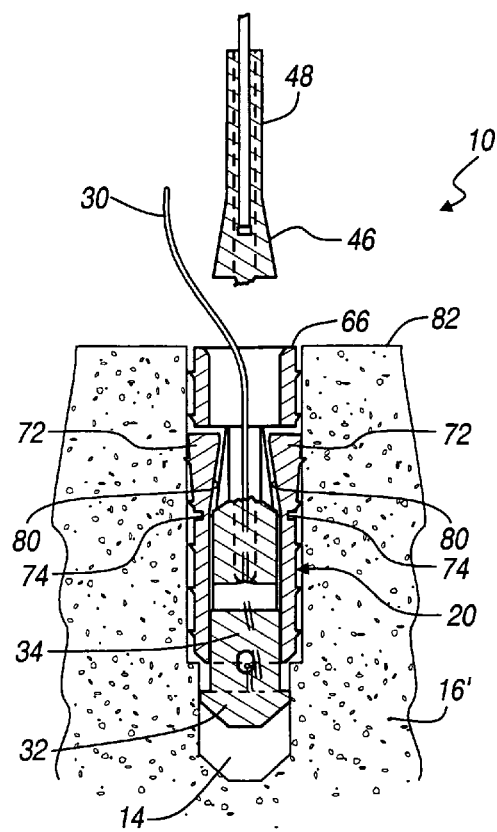
FIG. 5A is an environmental view illustrating an alternate use of the suture anchor of FIG. 1 after the application of a first retractive force.
Figure 5B:
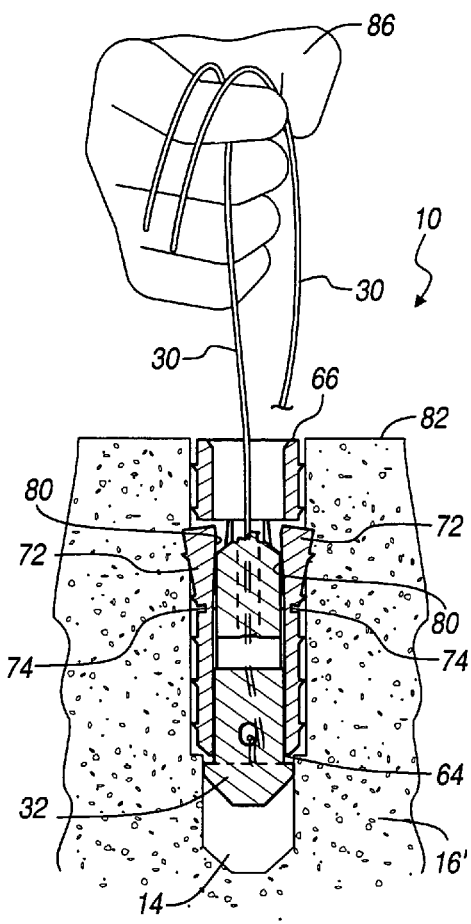
FIG. 5B is an environmental view of the suture anchor as a second retractive force is applied.

In a soft boney structure 16, when the expanding members 72 are fully engaged, the tip 32 of the suture receiving portion 22 is pressed against the first end 64 of the sleeve 20, and thus the insert 18 is not able to further retract. Hence, the continued application of the retractive force F1 causes the breakaway section 26 to fracture, as shown in FIG. 4C. With reference now to FIG. 5A, in a hard boney structure 16', however, the breakaway section 26 may fracture prior to the tip 32 of the suture receiving portion 22 contacting the first end 64 of the sleeve 20. In this situation, the suture 30 can be pulled by a hand 86 of an operator, as illustrated in FIG. 5B, such that the tip 32 of the suture receiving portion 22 abuts the first end 64 of the sleeve 20. The pulling of the suture 30 by the hand 86 of the operator causes the expanding members 72 to expand further due to the force applied to the tapered interior bearing surface 80 of the expanding members 72 by the cylindrical body 34 of the suture receiving portion 22. In either hard or soft boney structures 16, 16' once the breakaway section 26 fractures, the sleeve 20 and suture receiving portion 22 remain in the pre-drilled hole 14 to couple a selected soft tissue to the boney structures 16, 16' via the suture 30.

Figure 6A:
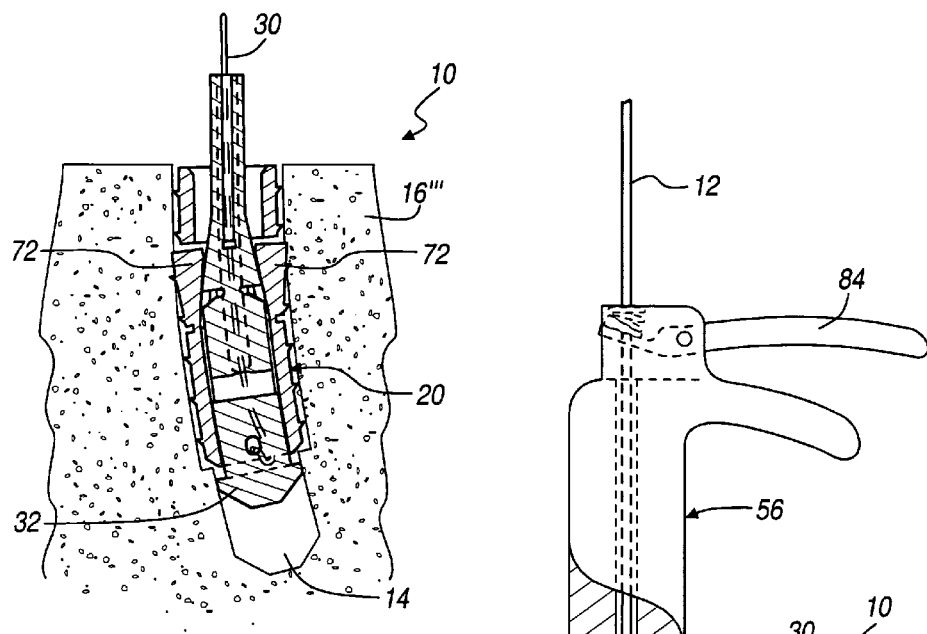
FIG. 6A is an alternate environmental view of a use of the suture anchor of FIG. 1.
Figure 6B:
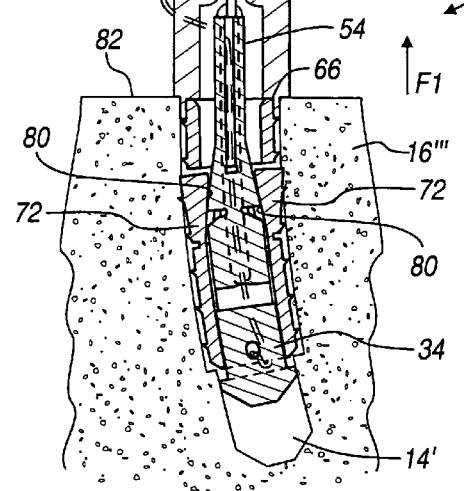
FIG. 6B is an environmental view of the suture anchor of FIG. 6A during the application of a retractive force.

In addition, the suture anchor 10 is also adaptable for use in a curved pre-drilled hole 14', as shown in FIG. 6A. In this exemplary embodiment, the suture anchor 10 may be positioned in the curved pre-drilled hole 14' via the actuator pin 12. Next, as shown in FIG. 6B, the retractive force F1 may be applied to the actuator pin 12 by an actuating device, such as the actuator gun 56, to cause the expanding members 72 to engage the boney structure 16''', as discussed previously.

Figures 7, 8:
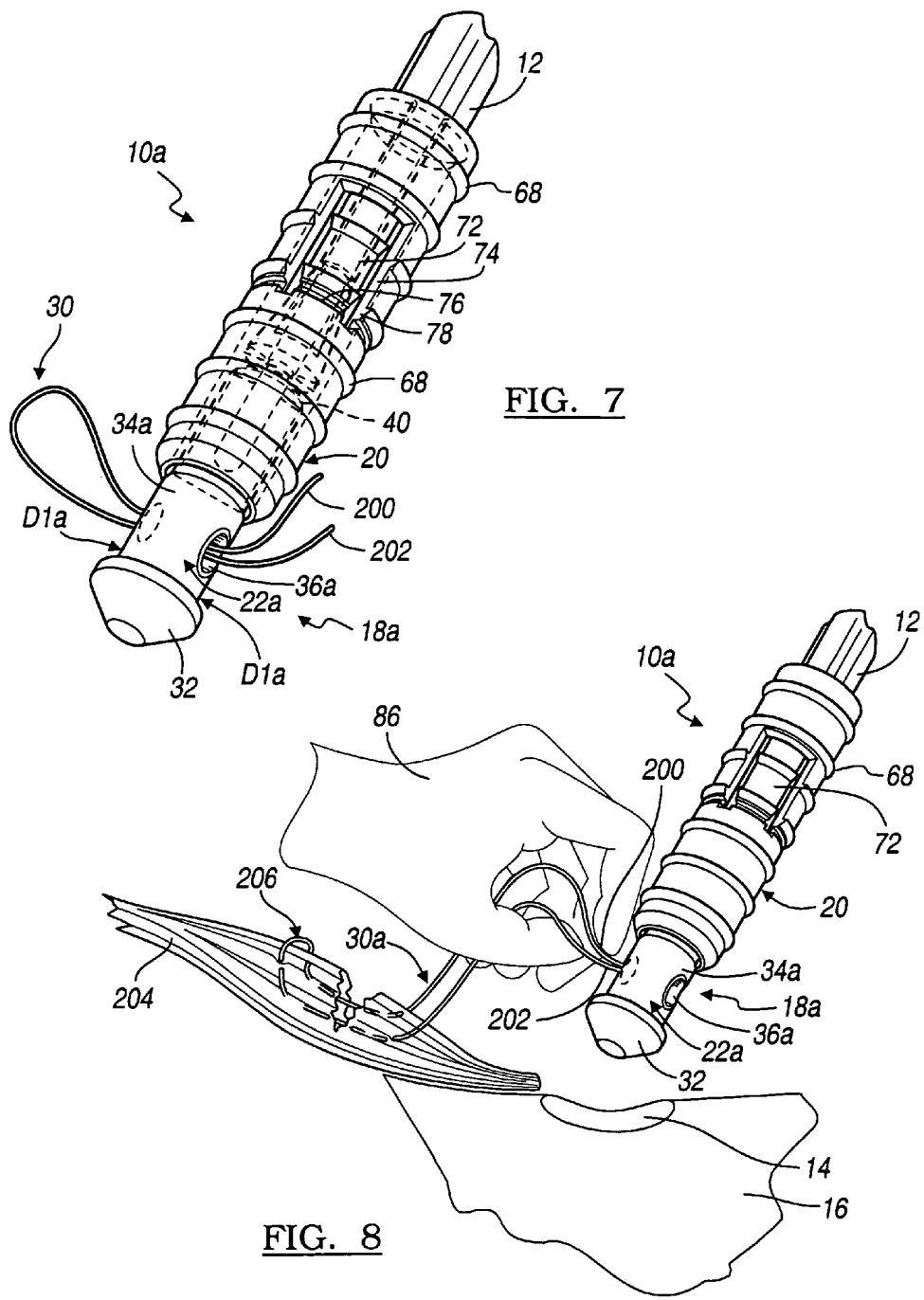
FIG. 7 is a perspective view of a first alternative expanding suture anchor having an actuator pin according to the present disclosure.
FIG. 8 is an environmental view of a first procedure associated with the suture anchor shown in FIG. 7.

With reference to FIG. 7, a first alternative insert 18a is shown. The first alternative insert 18a can include a suture receiving portion 22a, the breakaway section 26 and the end section 24 for use with a suture anchor 10a substantially similar to that described with regard to FIGS. 1-6B. As will be appreciated, the remainder of the suture anchor 10a can be generally similar to the suture anchor 10 that is illustrated in and described in conjunction with FIGS. 1-6B. In addition, as the breakaway section 26 and end section 24 of the first alternative insert 18a are substantially similar to the breakaway section 26 and end section 24 of the insert 18 of the suture anchor 10, the breakaway section 26 and end section 24 will not be discussed in detail with regard to the first alternative insert 18a. Further, the same reference numerals will be used to denote the same or similar components.

The suture receiving portion 22a and end section 24 can have a tensile and a torsion strength that are greater than the tensile and torsion strength of the breakaway section 26 such that the suture receiving portion 22a and end section 24 will be severed by the breakaway section 26 without damage to the structural integrity of either section. The first alternative insert 18a is generally insert molded from a resorbable material (such as, for example, Lactosorb® available from Biomet Inc. of Warsaw, Ind.); however, it will be understood that other types of biocompatible materials and other methods of forming could be used.

As shown in FIG. 7, the suture receiving portion 22a can include the tip 32, a cylindrical body 34a, and a suture 30a. The tip 32 can be generally conical in shape; however, any other desired shape may be used, such as rectangular. The cylindrical body 34a can have a diameter D1a, which is sized to ensure a slip fit with the sleeve 20 such that the cylindrical body 34a can slide within the sleeve 20. The cylindrical body 34a can define an aperture, which can be an eyelet 36a, extending through the cylindrical body 34a to provide an attachment point for the suture 30a. The diameter D1a of the cylindrical body 34a can also provide an interference fit between the cylindrical body 34a, the suture 30a and the sleeve 20. The cylindrical body 34a can further include the tapered section 40 leading to the breakaway section 26. The suture 30a can have a first end 200, a midsection 201 and a second end 202. The eyelet 36a can be sized to receive both the first end 200 and the second end 202 of the suture 30a. The suture 30a can be fixed to the cylindrical body 34a without the use of a knot by the sleeve 20, as will be discussed herein. The midsection 201 of the suture 30a can be coupled to a section of soft tissue 204, as shown in FIG. 8. The midsection 201 of the suture 30a can be coupled to the soft tissue 204 through any appropriate technique, such as a mattress stitch 206 or by using a suture punch (not shown).

In order to employ the suture anchor 10a, with the pre-drilled hole 14 drilled into the boney structure 16, the suture 30a can be coupled to the soft tissue 204. Then, the hand 86 of the operator can thread or insert the first end 200 and the second end 202 of the suture 30a through the eyelet 36a. With additional reference to FIG. 9, once the first end 200 and the second end 202 of the suture 30a are threaded through the eyelet 36a, the suture anchor 10a can be inserted into the pre-drilled hole 14. Generally, the first end 200 and the second end 202 of the suture 30a can extend beyond the pre-drilled hole 14 to enable the hand 86 of the operator to grasp either or both the first end 200 and the second end 202. The hand 86 of the operator can be used to tighten the suture 30a, and thus the soft tissue 204, to the pre-drilled hole 14 by pulling the first end 200 and second end 202 of the suture 30a that extends from the pre-drilled hole 14. This further removes any slack from the suture 30a. After the suture 30a is tightened, the expanding members 72 of the suture anchor 10a can be expanded to engage the pre-drilled hole 14.

Figure 9:
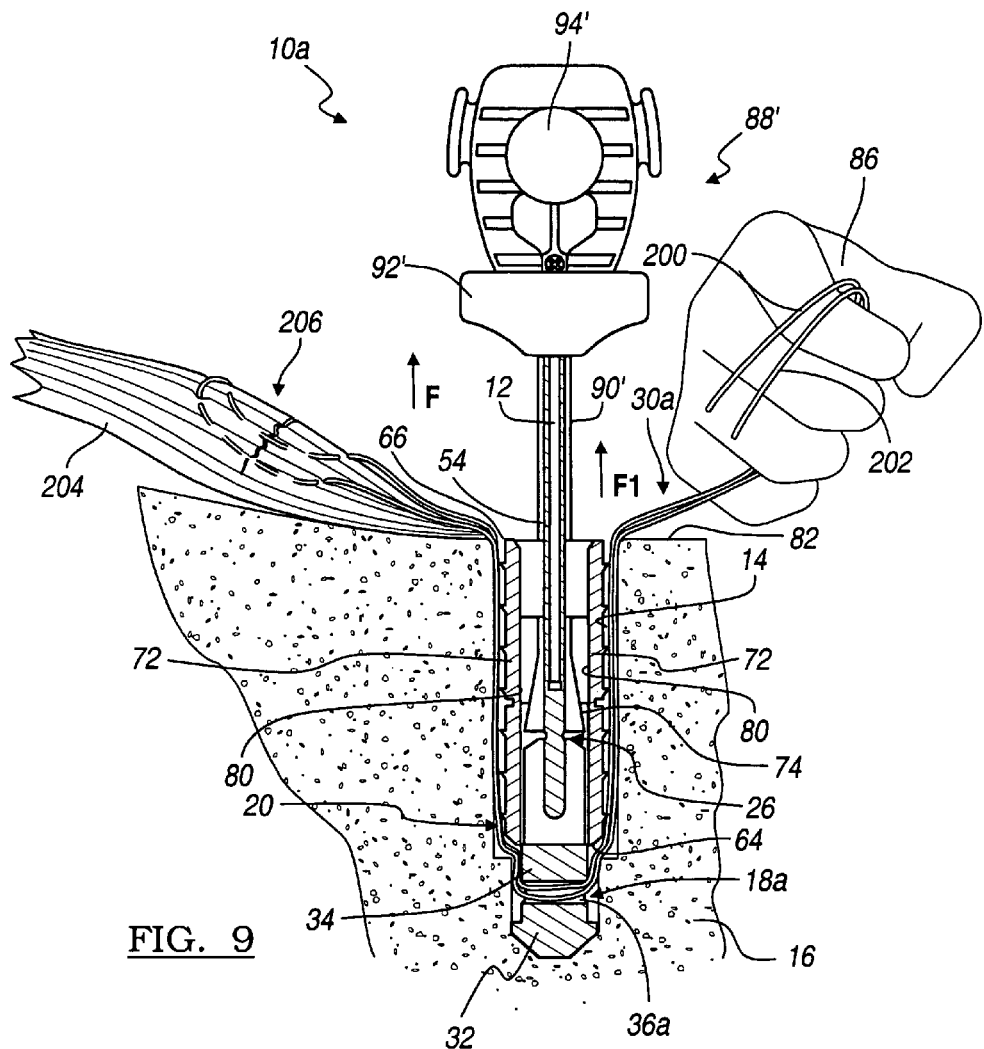
FIG. 9 is an environmental view of a second procedure associated with the suture anchor shown in FIG. 7.
Figure 10:
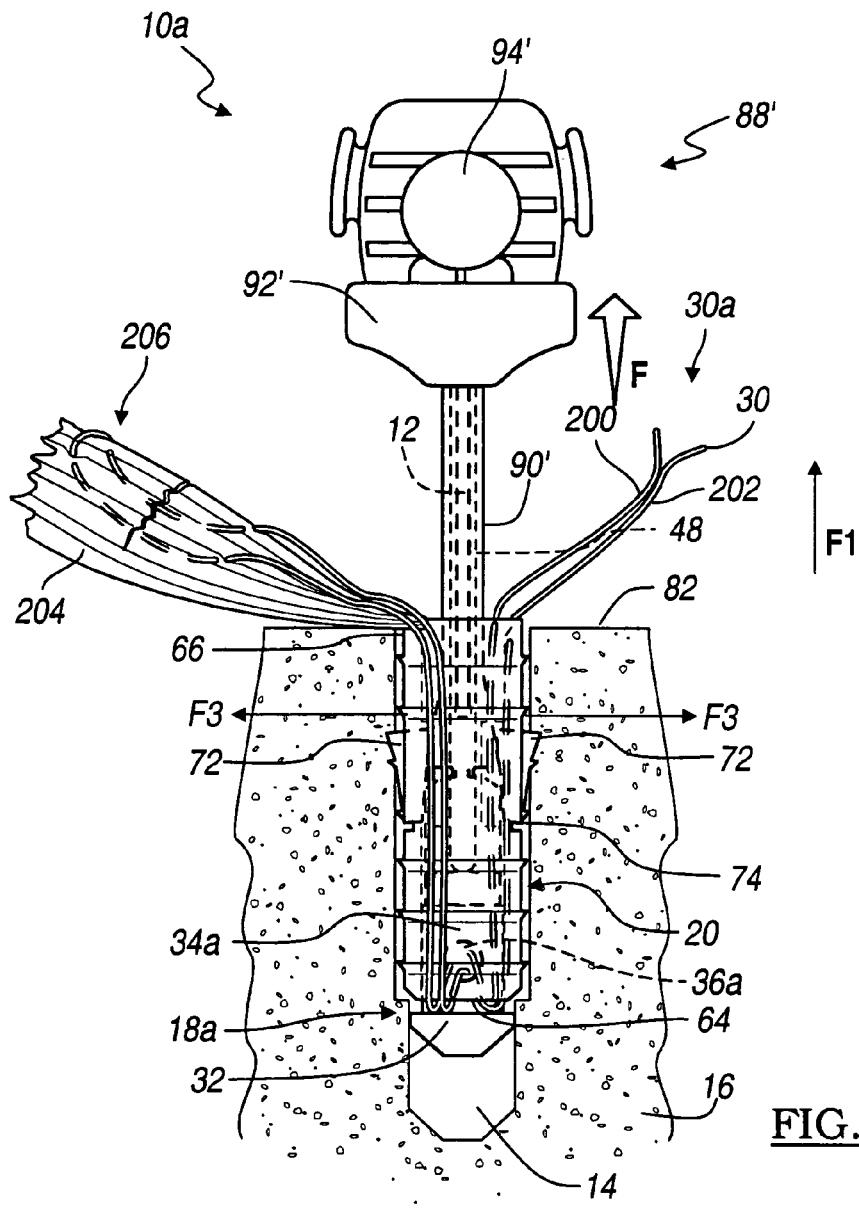
FIG. 10 is an environmental view of the suture anchor of FIG. 7 as the retractive force is applied to move the suture anchor into the fully expanded position.

For example, in order to expand the expanding members 72, an alternative syringe-type actuator 88' can be coupled to the actuator pin 12 of the suture anchor 10a as shown in FIGS. 9 and 10. The alternative syringe-type actuator 88' can include a cannula 90' that engages the actuator pin 12. A lever 92' can be used to retract the cannula 90' by the application of a force F to the lever 92'. Generally, the lever 92' can operate to retract the cannula 90' once it is engaged with the actuator pin 12 to provide the retractive force F1 to the suture anchor 10a. A safety or stop 94' can also be provided to prevent the operator from prematurely applying the retractive force F1.

In order to deploy the suture anchor 10a in the pre-drilled hole 14, the stop 94' can be pushed in and then the force F can be applied to the lever 92' on the syringe-type actuator 88', as shown in FIG. 10. When the lever 92' on the alternative syringe-type actuator 88' is pulled, the alternative syringe-type actuator 88' can apply the retractive force F1 to the actuator pin 12 via the cannula 90'. It should be noted, however, that the alternative syringe-type actuator 88' is not the only actuating device capable of applying the retractive force F1 to the suture anchor 10a. Numerous other devices can be employed, such as, a syringe-type actuator 88, as discussed with regard to FIG. 4D, or the actuator gun 56 discussed with regard to FIGS. 4A and 4B.

The application of the retractive force F1 can cause the first alternative insert 18a to be displaced or moved rearwardly with respect to the sleeve 20, as illustrated in FIG. 10. This rearward movement can cause the tapered portion 46 of the first alternative insert 18a to apply a force F3 to the tapered interior bearing surface 80 of the expanding members 72 of the sleeve 20. The first alternative insert 18a can continue to move rearward, which can cause the tapered portion 46 to apply an increasingly greater force F3 to the tapered interior bearing surface 80 of the expanding members 72 until the expanding members 72 are engaged with the boney structure 16.

When the expanding members 72 are fully engaged, the tip 32 of the suture receiving portion 22a can be adjacent to the suture 30a, while the suture 30a is adjacent to the first end 64 of the sleeve 20 (as best shown in FIG. 12). The compression of the suture 30a between the suture receiving portion 22a and the tip 32 can fix or lock the suture 30a to the suture anchor 10a, while preventing the first alternative insert 18a from retracting further. The continued application of the retractive force F1 to the first alternative insert 18a can cause the breakaway section 26 to fracture, as shown in FIG. 11.

It should be noted, as shown in FIG. 11A, the pre-drilled hole 14 can be sized with a depth D substantially equivalent to a length L of the suture anchor 10a, if desired. If the pre-drilled hole 14 has the depth D substantially equivalent to the length L of the suture anchor 10a, then the expanding members 72 can be deployed or expanded by the contact of the tip 32 of the suture receiving portion 22a against a bottom 213 of the pre-drilled hole 14. Generally, as the suture anchor 10a is inserted, the tip 32 can be pushed against the bottom 213 of the pre-drilled hole 14, forcing the first alternative insert 18a to be displaced or moved rearwardly with respect to the sleeve 20. This rearward movement can cause the tapered portion 46 of the first alternative insert 18a to apply a force F3 to the tapered interior bearing surface 80 of the expanding members 72 of the sleeve 20. Then, the lever 92' on the syringe-type actuator 88' can be pulled (with the stop 94' pushed in) to apply the retractive force F1 to the actuator pin 12 to fully engage the expanding members 72 in the pre-drilled hole 14. The continued application of the retractive force F1 to the first alternative insert 18a can cause the breakaway section 26 to fracture, as shown in FIG. 11.

Once the breakaway section 26 fractures, as shown in either FIG. 11 or 11A, the sleeve 20 and suture receiving portion 22a remain in the pre-drilled hole 14 to couple the soft tissue 204 to the boney structure 16 via the suture 30a. The first end 200 and second end 202 of the suture 30a that extends from the pre-drilled hole 14 can then be trimmed if desired (not shown).

As shown in FIG. 12, the suture anchor 10a can fix the suture 30a to the suture anchor 10a without the use of a knot. Generally, as the first end 200 and second end 202 of the suture 30a extend from the eyelet 36a of the first alternative insert 18a prior to the deployment of the expanding members 72 of the sleeve 20, the application of the retractive force F1 causes the first alternative insert 18a, and thus suture 30a, to be withdrawn into the sleeve 20. Thus, the movement of the first alternative insert 18a within the sleeve 20 can fix or lock the suture 30a to the suture anchor 10a due to the interference fit between the first alternative insert 18a, the suture 30a and the sleeve 20. Further, the interference fit between the first alternative insert 18a, the suture 30a and the sleeve 20 can prevent the first alternative insert 18a from moving after the deployment of the expanding members 72 due to the frictional lock created between the suture 30a, the first alternative insert 18a and the sleeve 20.

Figures 13, 14:
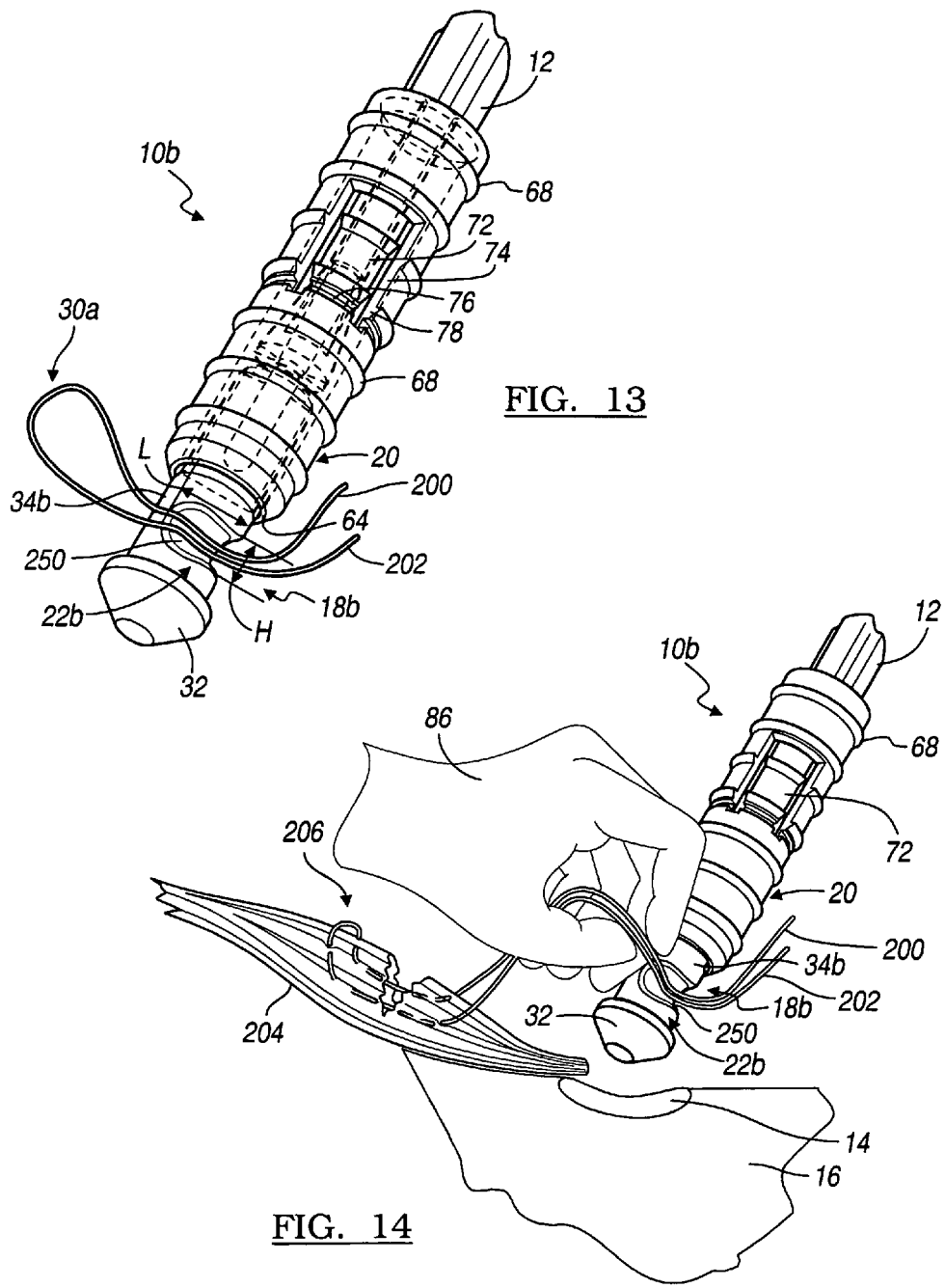
FIG. 13 is a perspective view of a second alternative expanding suture anchor having an actuator pin according to the present disclosure.
FIG. 14 is an environmental view of a first procedure associated with the suture anchor shown in FIG. 13.

With reference to FIG. 13, a second alternative insert 18b is shown. The second alternative insert 18b can include a suture receiving portion 22b, the breakaway section 26, and the end section 24 for use with a suture anchor 10b substantially similar to that described with regard to FIGS. 7-12. As the breakaway section 26 and end section 24 of the second alternative insert 18b are substantially similar to the breakaway section 26 and end section 24 of the insert 18, the breakaway section 26 and end section 24 will not be discussed in detail with regard to the second alternative insert 18b. In addition, as the suture receiving portion 22b is substantially similar to the suture receiving portion 22a of the first alternative insert 18a, as discussed with FIGS. 7-12, only the modifications to the suture receiving portion 22b will be discussed herein.

As shown in FIG. 13, the suture receiving portion 22b can include an aperture, for example, a groove or slot 250, which can be for receipt of the suture 30a. Generally, the slot 250 can be formed longitudinally in a cylindrical body 34b of the second alternative insert 18b; however, the slot 250 can be formed in any desired position, such as vertically or diagonally. As will be appreciated, the remainder of the cylindrical body 34b can be generally similar to the cylindrical body 34a that is illustrated in and described in conjunction with FIG. 7.

The slot 250 can extend for a length L and can have a height H configured to enable an operator to insert the first end 200 and second end 202 of the suture 30a through the slot 250, as shown in FIG. 14. Generally, once the midsection 201 of the suture 30a is coupled to the soft tissue 204 via the mattress stitch 206 or any other technique, such as a suture punch (not shown), the hand 86 of the operator can thread or insert the first end 200 and second end 202 of the suture 30a into the slot 250. Then, with reference to FIG. 15, the suture anchor 10b can be inserted into the pre-drilled hole 14. As discussed previously, the hand 86 of the operator can be used to tighten the suture 30a, and thus the soft tissue 204, to the pre-drilled hole 14 by pulling the first end 200 and second end 202 of the suture 30a that extends from the pre-drilled hole 14. After the suture 30a is tightened, the suture anchor 10b can be deployed to engage the pre-drilled hole 14 through the use of the actuator gun 56, syringe-type actuator 88 or syringe-type actuator 88', for example, as discussed previously with reference to FIGS. 4A and 4B, 4D and 9-12, respectively.

Figure 16:
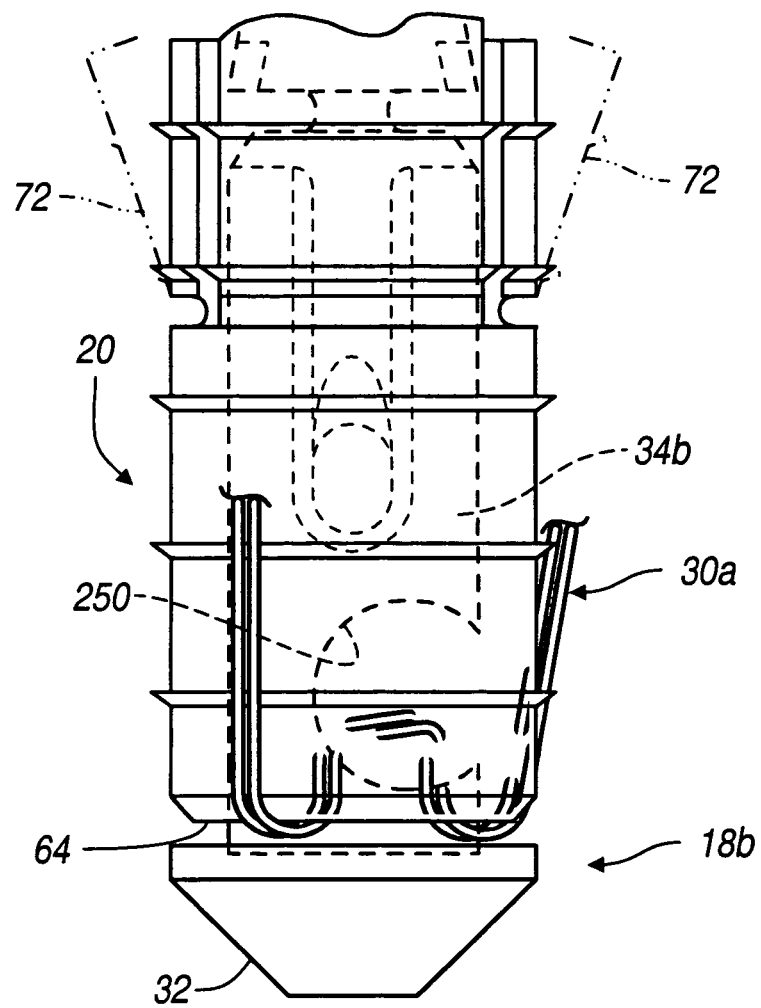
FIG. 16 is detailed front view of the suture anchor of FIG. 13 illustrating a suture fixed to the suture anchor.

When the suture anchor 10b is fully engaged to the pre-drilled hole 14, the tip 32 of the suture receiving portion 22b can be adjacent to the suture 30a, while the suture 30a is adjacent to the first end 64 of the sleeve 20 (as best shown in FIG. 16). The compression of the suture 30a between the suture receiving portion 22b and the tip 32 can fix or lock the suture 30a to the suture anchor 10b. Thus, the suture anchor 10b can also fix the suture 30a to the suture anchor 10b without the use of a knot, while providing greater access for the hand 86 of the operator to couple the first end 200 and the second end 202 to the second alternative insert 18b prior to the placement of the suture anchor 10b into the pre-drilled hole 14. The first end 200 and second end 202 of the suture 30a that extends from the pre-drilled hole 14 can then be trimmed if desired (not shown).

Figures 17, 18:
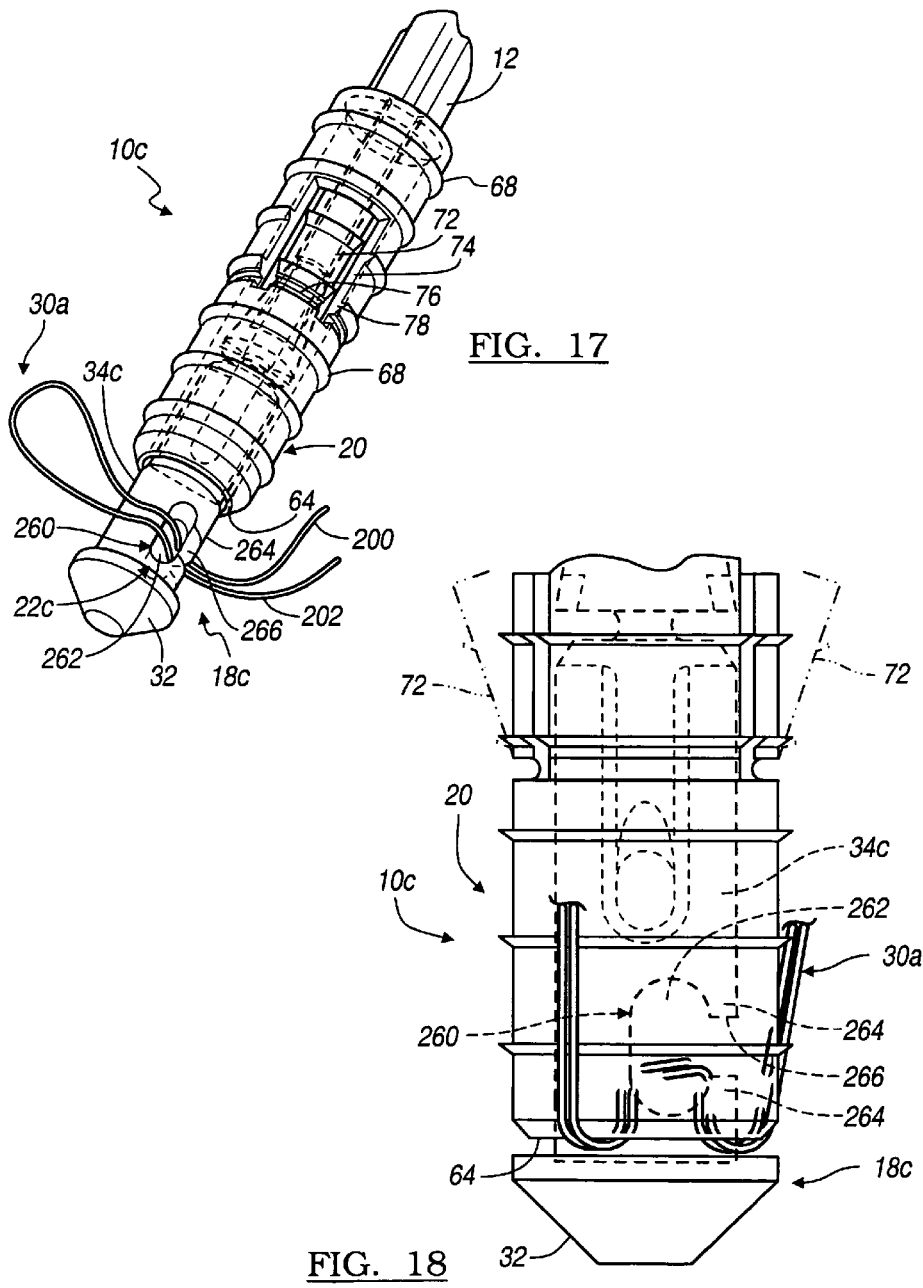
FIG. 17 is a perspective view of a third alternative expanding suture anchor having an actuator pin according to the present disclosure.
FIG. 18 is detailed front view of the suture anchor of FIG. 17 illustrating a suture fixed to the suture anchor.

With reference to FIG. 17, a third alternative insert 18c is shown. The third alternative insert 18c can include a suture receiving portion 22c, the breakaway section 26, and the end section 24 for use with a suture anchor 10c substantially similar to that described with regard to FIGS. 7-12. As the breakaway section 26 and end section 24 of the third alternative insert 18c are substantially similar to the breakaway section 26 and end section 24 of the insert 18, the breakaway section 26 and end section 24 will not be discussed in detail with regard to the third alternative insert 18c. In addition, as the suture receiving portion 22c is substantially similar to the suture receiving portion 22a of the first alternative insert 18a, as discussed with FIGS. 7-12, only the modifications to the suture receiving portion 22c will be discussed herein.

As shown in FIG. 17, the suture receiving portion 22c can include a slot, for example, a C-shaped slot 260, which can be for receipt of the suture 30a. Generally, the slot 260 can be defined in a cylindrical body 34c of the third alternative insert 18c. As will be appreciated, the remainder of the cylindrical body 34c can be generally similar to the cylindrical body 34a that is illustrated in and described in conjunction with FIG. 7. The slot 260 can define a throughbore 262 and a necked portion 264 as shown in FIGS. 17 and 18. The necked portion 264 can define an aperture 266 for receipt of the first end 200 and second end 202 of the suture 30a. Generally, the necked portion 264 can be configured such that the first end 200 and second end 202 of the suture 30a can be hooked behind and retained by the necked portion 264.

Figure 15:
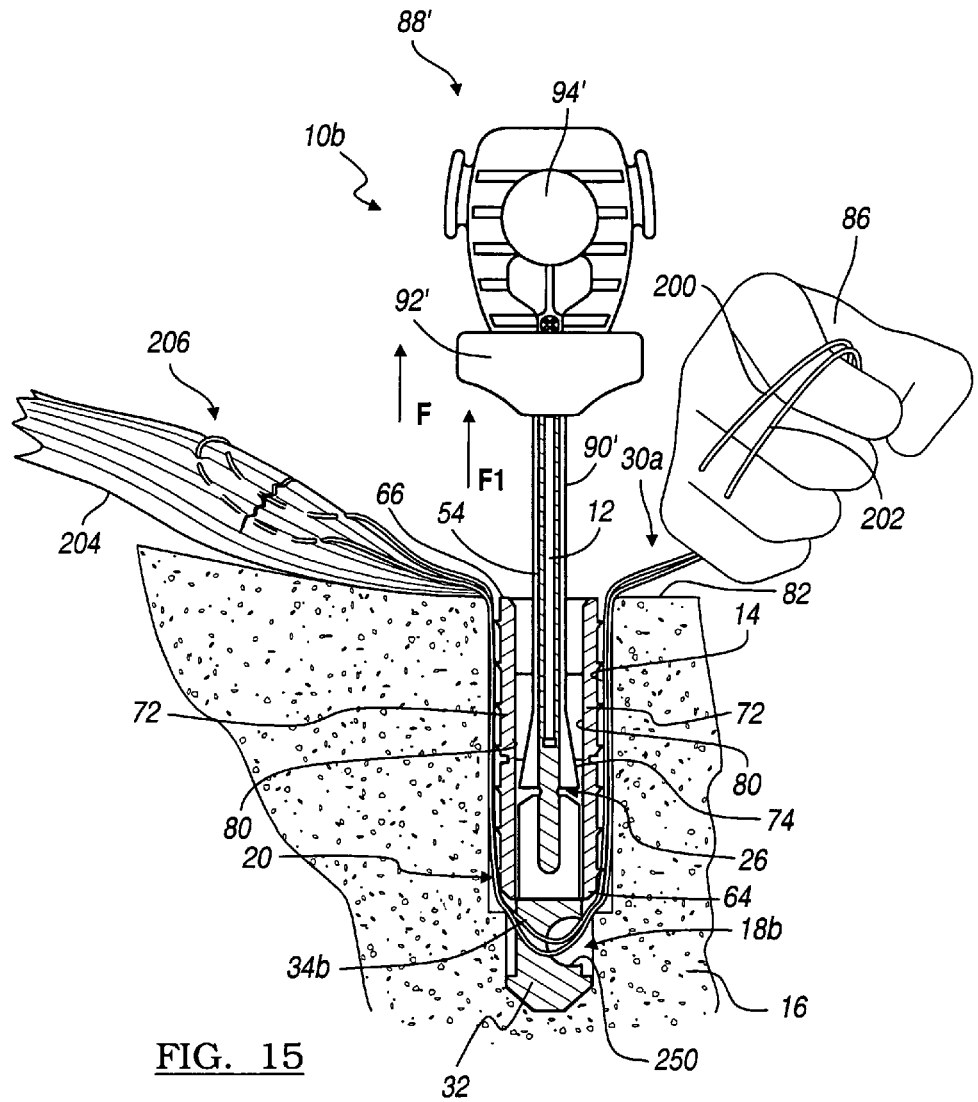
FIG. 15 is an environmental view of a second procedure associated with the suture anchor shown in FIG. 13.

As the assembly and deployment of the suture anchor 10c can be substantially similar to the assembly and deployment of the suture anchor 10a discussed with regard to FIGS. 8-12 and the suture anchor 10b discussed with regard to FIGS. 15 and 16, the assembly and deployment of the suture anchor 10c will not be discussed in detail herein. Briefly, however, once the midsection 201 of the suture 30a is coupled to the soft tissue 204 via the mattress stitch 206 or any other technique, such as a suture punch (not shown), the hand 86 of the operator can thread or insert the first end 200 and second end 202 of the suture 30a through the aperture 266 of the necked portion 264 and into the throughbore 262 (not shown). Then, the suture anchor 10c can be inserted into the pre-drilled hole 14. The hand 86 of the operator can be used to tighten the suture 30a, and thus the soft tissue 204, to the pre-drilled hole 14 by pulling the first end 200 and second end 202 of the suture 30a that extends from the pre-drilled hole 14 (not shown). This further removes any slack from the suture 30a. After the suture 30a is tightened, the expanding members 72 of the suture anchor 10c can be deployed or expanded to engage the pre-drilled hole 14.

When the suture anchor 10c is fully engaged to the pre-drilled hole 14, the tip 32 of the suture receiving portion 22c can be adjacent to the suture 30a, while the suture 30a is adjacent to the first end 64 of the sleeve 20 (as best shown in FIG. 18). The compression of the suture 30a between the suture receiving portion 22c and the tip 32 can fix or lock the suture 30a to the suture anchor 10c. Thus, the suture anchor 10c can also fix the suture 30a to the suture anchor 10c without the use of a knot. The first end 200 and second end 202 of the suture 30a that extends from the pre-drilled hole 14 can then be trimmed if desired (not shown).

With reference to FIG. 19, a fourth alternative insert 18d is shown. The fourth alternative insert 18d can include a suture receiving portion 22d, the breakaway section 26, and the end section 24 for use with a suture anchor 10d substantially similar to that described with regard to FIGS. 7-12. As the breakaway section 26 and end section 24 of the fourth alternative insert 18d are substantially similar to the breakaway section 26 and end section 24 of the insert 18, the breakaway section 26 and end section 24 will not be discussed in detail with regard to the fourth alternative insert 18d. In addition, as the suture receiving portion 22d is substantially similar to the suture receiving portion 22a of the first alternative insert 18a, as discussed with FIGS. 7-12, only the modifications to the suture receiving portion 22d will be discussed herein.

As shown in FIG. 19, the suture receiving portion 22d can include a hinged slot 270 which can be for receipt of the suture 30a. Generally, the hinged slot 270 can be defined in a cylindrical body 34d of the fourth alternative insert 18d. As will be appreciated, the remainder of the cylindrical body 34d can be generally similar to the cylindrical body 34a that is illustrated in and described in conjunction with FIG. 7.

The hinged slot 270 can define a throughbore 272 and can include a hinged portion 274. The hinged portion 274 can optionally include at least one or a plurality of barbs or projections 276. The throughbore 272 can be configured to retain the first end 200 and second end 202 of the suture 30a. The hinged portion 274 can be pivotably coupled to the cylindrical body 34d and can rotate from an opened position to a closed position. In the opened position, as shown in FIG. 19, the hinged portion 274 can define an aperture 278 for receipt of the first end 200 and second end 202 of the suture 30a to enable the suture 30a to enter the throughbore 272 of the hinged slot 270. In the closed position, the hinged portion 274 can seal or enclose the aperture 278 to retain the suture 30a within the throughbore 272, as shown in FIG. 20. Thus, generally, the hinged portion 274 can be sized such that in the closed position the hinged portion 274 can substantially enclose the aperture 278. The projections 276 of the hinged portion 274 are optional and can be coupled to or formed with the hinged portion 274 if desired. The projections 276 can extend into the throughbore 272 when the hinged portion 274 is in the closed position to further retain the suture 30a within the throughbore 272. The projections 276 are illustrated as triangular, however, any appropriate shape, such as annular or hooked, could be employed.

As the assembly and deployment of the suture anchor 10d in the pre-drilled hole 14 is substantially similar to the assembly and deployment of the suture anchor 10a discussed with regard to FIGS. 8-12 and the suture anchor 10b discussed with regard to FIGS. 15 and 16, the assembly and deployment of the suture anchor 10d will not be discussed in detail herein. Briefly, however, once the midsection 201 of the suture 30a is coupled to the soft tissue 204 via the mattress stitch 206 or any other technique, such as a suture punch, the hand 86 of the operator can thread or insert the first end 200 and second end 202 of the suture 30a through the aperture 278 of the hinged portion 274 and into the throughbore 272 (not shown). Then, the suture anchor 10d can be inserted into the pre-drilled hole 14 (not shown). The hand 86 of the operator can be used to tighten the suture 30a, and thus the soft tissue 204, to the pre-drilled hole 14 by pulling the first end 200 and second end 202 of the suture 30a that extends from the pre-drilled hole 14 (not shown). This further removes any slack from the suture 30a. After the suture 30a is tightened, the expanding members 72 of the suture anchor 10d can be deployed to engage the pre-drilled hole 14. During the deployment of the suture anchor 10d, as the fourth alternative insert 18d moves rearwardly in the sleeve 20, the hinged portion 274 can be pushed closed by the sleeve 20 to lock the suture 30a within the throughbore 272 of the suture receiving portion 22d.

When the suture anchor 10d is fully engaged to the pre-drilled hole 14, the tip 32 of the suture receiving portion 22d can be adjacent to the suture 30a, while the suture 30a is adjacent to the first end 64 of the sleeve 20 (as best shown in FIG. 20). The compression of the suture 30a between the suture receiving portion 22d and the tip 32 can fix or lock the suture 30a to the suture anchor 10d. Thus, the suture anchor 10d can also fix the suture 30a to the suture anchor 10d without the use of a knot. The first end 200 and second end 202 of the suture 30a that extends from the pre-drilled hole 14 can then be trimmed if desired (not shown).

Figure 21:
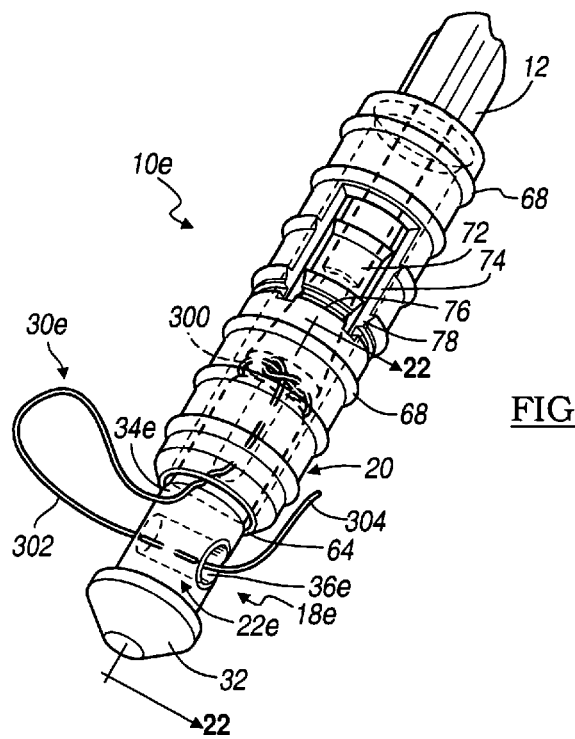
FIG. 21 is a perspective view of a fifth alternative expanding suture anchor having an actuator pin according to the present disclosure.

With reference to FIG. 21, a fifth alternative insert 18e is shown. The fifth alternative insert 18e can include a suture receiving portion 22e, the breakaway section 26, and the end section 24 for use with a suture anchor 10e substantially similar to that described with regard to FIGS. 1-6B. As will be appreciated, the remainder of the suture anchor 10e can be generally similar to the suture anchor 10 that is illustrated in and described in conjunction with FIGS. 1-6B. As the breakaway section 26 and end section 24 of the fifth alternative insert 18e are substantially similar to the breakaway section 26 and end section 24 of the insert 18, the breakaway section 26 and end section 24 will not be discussed in detail with regard to the fifth alternative insert 18e.

The suture receiving portion 22e and end section 24 can have a tensile and a torsion strength that are greater than the tensile and torsion strength of the breakaway section 26 such that the suture receiving portion 22e and end section 24 will be severed by the breakaway section 26 without damage to the structural integrity of either section. The fifth alternative insert 18e is generally insert molded from a resorbable material (such as, for example, Lactosorb® available from Biomet Inc. of Warsaw, Ind.); however, it will be understood that other types of biocompatible materials and other methods of forming could be used.

As shown in FIG. 21, the suture receiving portion 22e can include the tip 32, a cylindrical body 34e and a suture 30e. The tip 32 can be generally conical in shape; however, any other desired shape may be used, such as rectangular. The cylindrical body 34e can have a diameter D1e, which is sized to ensure a slip fit with the sleeve 20 such that the cylindrical body 34e can slide within the sleeve 20. The cylindrical body 34e can define an aperture or eyelet 36e extending through the cylindrical body 34e to provide an attachment point for the suture 30e. The cylindrical body 34e can further include the tapered section 40 leading to the breakaway section 26.

Figure 22:
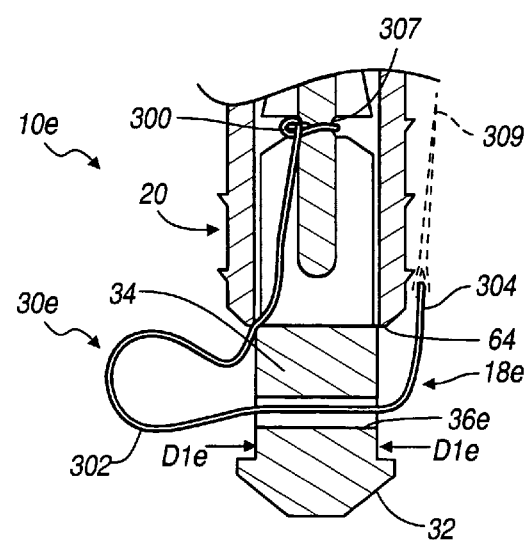
FIG. 22 is a cross-sectional view taken along line 22-22 of FIG. 21.
Figure 23:
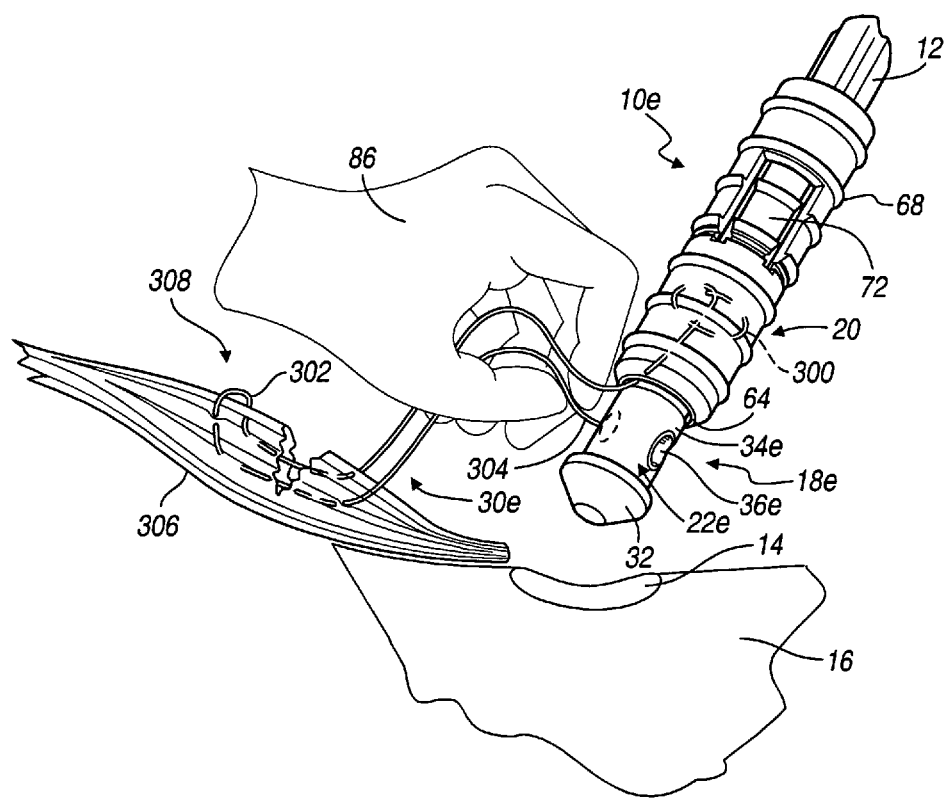
FIG. 23 is an environmental view of a first procedure associated with the suture anchor shown in FIG. 21.

With additional reference to FIGS. 22 and 23, the suture 30e can have a first end 300, a midsection 302 and a second end 304. The first end 300 of the suture 30e can be coupled to the breakaway section 26 of the fifth alternative insert 18e. Generally, the first end 300 can be knotted about the breakaway section 26 at a midpoint 307 of the two necked portions 42, 44 (FIG. 22). The midsection 302 of the suture 30e can be coupled to a section of soft tissue 306 (FIG. 23). The second end 304 of the suture 30e can be received into the eyelet 36e of the cylindrical body portion 34e of the fifth alternative insert 18e. The second end 304 can be coupled to a needle 309 (shown in phantom) to facilitate the threading of the second end 304 into the eyelet 36e (FIG. 22). The second end 304, once threaded, can pass through the eyelet 36e to secure the soft tissue 306 to the pre-drilled hole 14, as will be discussed in greater detail herein.

With reference to FIG. 23, prior to the assembly of the sleeve 20 with the fifth alternative insert 18e, the first end 300 of the suture 30e can be knotted to the midpoint 307 of the breakaway section 26 of the fifth alternative insert 18e. Then, the sleeve 20 can be disposed over the breakaway section 26 of the fifth alternative insert 18e, such that the second end 304 of the suture 30e can extend out from the sleeve 20. Then, with the pre-drilled hole 14 drilled into the boney structure 16, and the first end the suture 30e coupled to the breakaway section 26, the midsection 302 of the suture 30e can be coupled to the soft tissue 306. The suture 30e can be coupled to the soft tissue 306 through any appropriate technique, such as a mattress stitch 308 or a suture punch (not shown), for example. Then, the hand 86 of an operator can thread or insert the second end 304 of the suture 30e through the eyelet 36e with or without the use of the needle 309.

Figure 24:
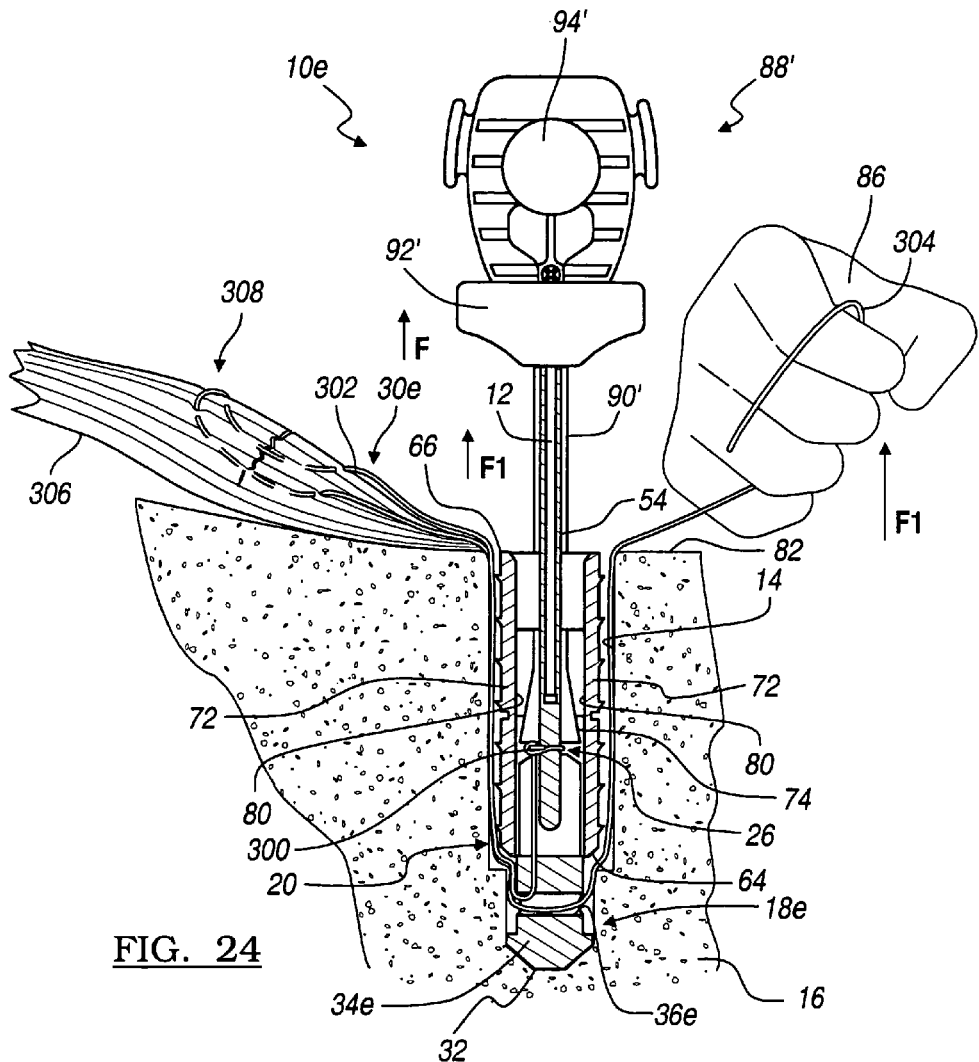
FIG. 24 is an environmental view of a second procedure associated with the suture anchor shown in FIG. 21.

With additional reference to FIG. 24, once the second end 304 of the suture 30e is threaded through the eyelet 36e, the suture anchor 10e can be inserted into the pre-drilled hole 14. Generally, the second end 304 of the suture 30e can extend beyond the pre-drilled hole 14 to enable the hand 86 of the operator to grasp the second end 304 to tighten the suture 30e, and thus the soft tissue 306, to the pre-drilled hole 14. Typically, the suture 30e can be tightened by pulling the second end 304 of the suture 30e that extends beyond the pre-drilled hole 14. This further removes any slack from the suture 30e. After the suture 30e is tightened, the expanding members 72 of the suture anchor 10e can be deployed to engage the pre-drilled hole 14.

Figure 25:
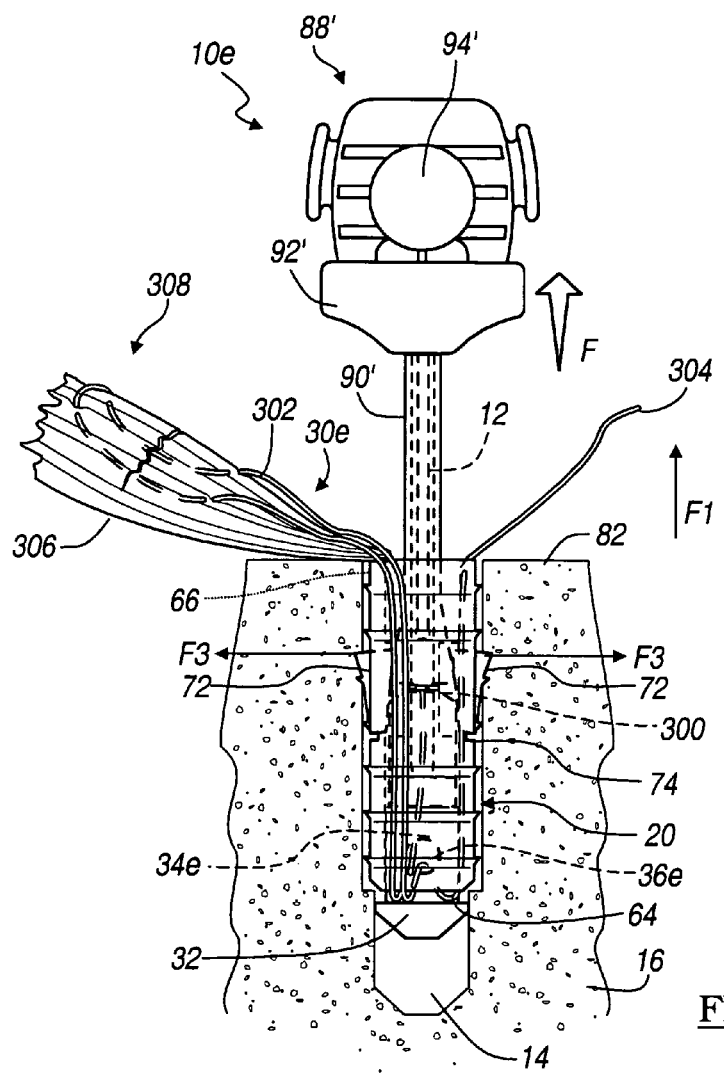
FIG. 25 is an environmental view of the suture anchor of FIG. 21 as the retractive force is applied to move the suture anchor into the fully expanded position.

As discussed herein, the alternative alternative syringe-type actuator 88' can be used to expand the expanding members 72 of the suture anchor 10e; however, any other activating device, such as the actuator gun 56 discussed with regard to FIGS. 4A and 4B, or the syringe-type actuator 88 discussed with regard to FIG. 4D, could be used. If the alternative alternative syringe-type actuator 88' is used, then the lever 92' on the alternative syringe-type actuator 88' can be pulled, as shown in FIG. 25, to apply the retractive force F1 to the actuator pin 12. The application of the retractive force F1 can cause the fifth alternative insert 18e to be displaced or moved rearwardly with respect to the sleeve 20 and can cause the tapered portion 46 of the fifth alternative insert 18e to apply a force F3 to the tapered interior bearing surface 80 of the expanding members 72 of the sleeve 20 until the expanding members 72 are engaged with the boney structure 16.

Figure 26:
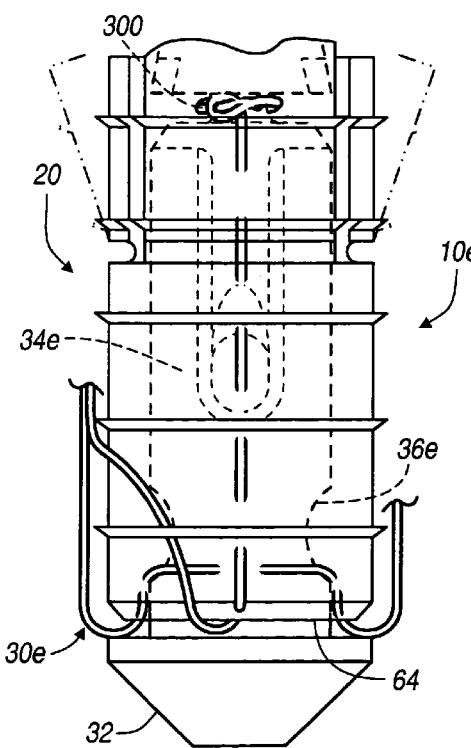
FIG. 26 is an environmental view illustrating the suture anchor of FIG. 21 in a fully expanded position.

When the expanding members 72 are fully engaged, the tip 32 of the suture receiving portion 22e can be adjacent to the suture 30e, while the suture 30e is adjacent to the first end 64 of the sleeve 20 (as best shown in FIG. 19). The compression of the suture 30e between the suture receiving portion 22e and the tip 32 can fix or lock the suture 30e to the suture anchor 10e, while preventing the fifth alternative insert 18e from retracting further. The continued application of the retractive force F1 to the fifth alternative insert 18e can cause the breakaway section 26 to fracture, as shown in FIG. 26. Once the breakaway section 26 fractures, the sleeve 20 and suture receiving portion 22e remain in the pre-drilled hole 14 to couple the soft tissue 306 to the boney structure 16 via the suture 30e. The portion of the second end 304 that extends from the pre-drilled hole 14 can then be trimmed if desired (not shown).

Figure 27:
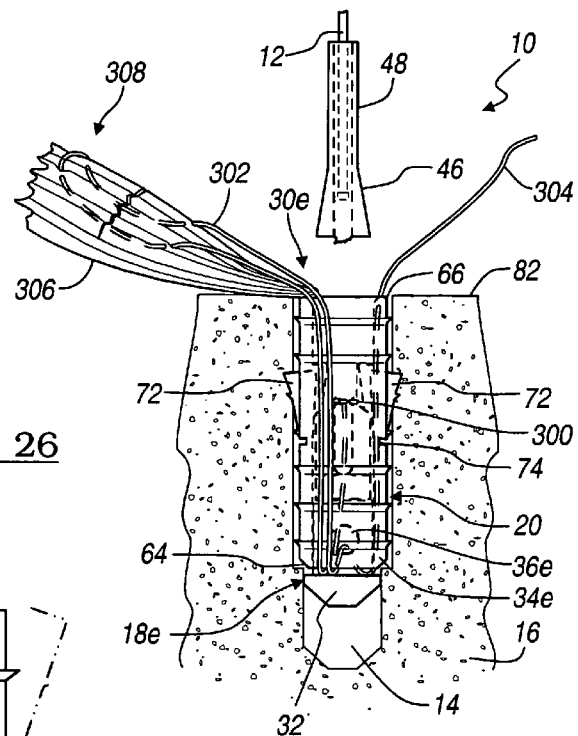
FIG. 27 is detailed front view of the suture anchor of FIG. 21 illustrating a suture fixed to the suture anchor.

As shown in FIG. 27, the suture anchor 10e can fix or lock the second end 304 of the suture 30e to the suture anchor 10e without the use of a knot. In addition, the suture anchor 10e can ensure the first end 300 of the suture 30e remains fixed to the fifth alternative insert 18e. Generally, as a portion of the first end 300 extends from the sleeve 20 and the second end 304 extends from the eyelet 36e of the fifth alternative insert 18e prior to the deployment of the expanding members 72 of the sleeve 20, the application of the retractive force F1 causes the fifth alternative insert 18e, and thus the portion of the first end 300 and the second end 304 extending from the eyelet 36e, to be withdrawn into the sleeve 20. Thus, the movement of the fifth alternative insert 18e within the sleeve 20 can fix or lock the portion of the first end 300 and the second end 304 to the suture anchor 10e due to the interference fit between the fifth alternative insert 18e, the suture 30e, and the sleeve 20, as discussed previously. Additionally, the frictional lock created between the suture 30e, the fifth alternative insert 18e and the sleeve 20 can prevent the fifth alternative insert 18e from moving after the deployment of the expanding members.

Figures 28, 29:
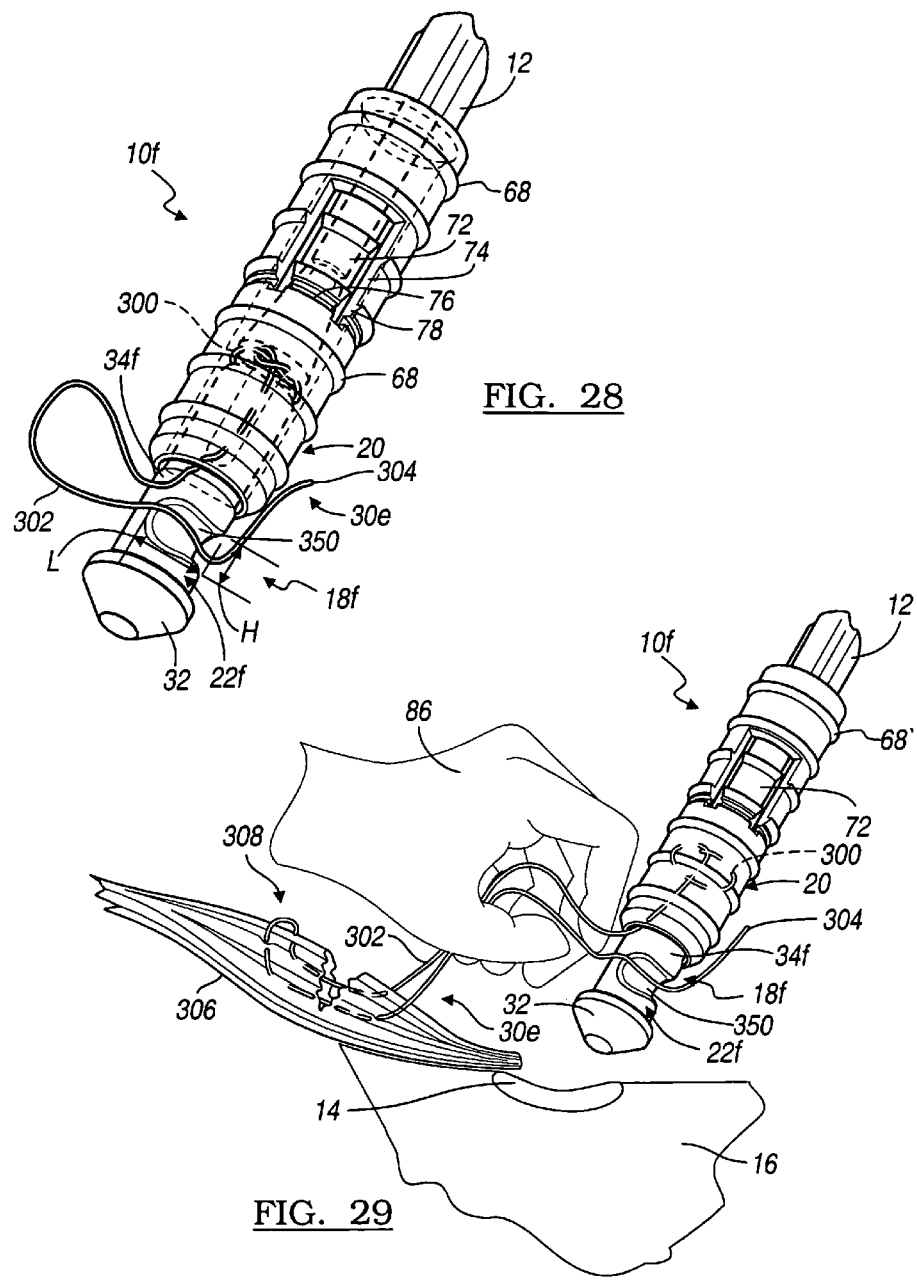
FIG. 28 is a perspective view of a sixth alternative expanding suture anchor having an actuator pin according to the present disclosure.
FIG. 29 is an environmental view of a first procedure associated with the suture anchor shown in FIG. 28.

With reference to FIG. 28, a sixth alternative insert 18f is shown. The sixth alternative insert 18f can include a suture receiving portion 22f, the breakaway section 26, and the end section 24 for use with a suture anchor 10f substantially similar to the suture anchor 10e described with regard to FIGS. 21-27. As the breakaway section 26 and end section 24 of the sixth alternative insert 18f are substantially similar to the breakaway section 26 and end section 24 of the insert 18, the breakaway section 26 and end section 24 will not be discussed in detail with regard to the sixth alternative insert 18f. In addition, as the suture receiving portion 22f is substantially similar to the suture receiving portion 22e of the fifth alternative insert 18e, as discussed with reference to FIGS. 21-27, only the modifications to the suture receiving portion 22f will be discussed herein.

As shown in FIG. 28, the suture receiving portion 22f can include an aperture, for example, a groove or slot 350, which can be for receipt of the suture 30e. Generally, the slot 350 can be formed longitudinally in a cylindrical body 34f of the sixth alternative insert 18f; however, the slot 350 can be formed in any desired position, such as vertically or diagonally. As will be appreciated, the remainder of the cylindrical body 34f can be generally similar to the cylindrical body 34*e* that is illustrated in and described in conjunction with FIG. 21.

The slot 350 can extend for a length L and can have a height H configured to enable an operator to insert the second end 304 of the suture 30*e* through the slot 350, as shown in FIG. 29. Generally, once the first end 300 of the suture 30*e* is tied to the breakaway section 26 and the midsection 302 of the suture 30*e* is coupled to the soft tissue 306 via the mattress stitch 308 or any other technique, such as a suture punch (not shown), the hand 86 of the operator can thread or insert the second end 304 of the suture 30*e* into the slot 350.

Figure 30:
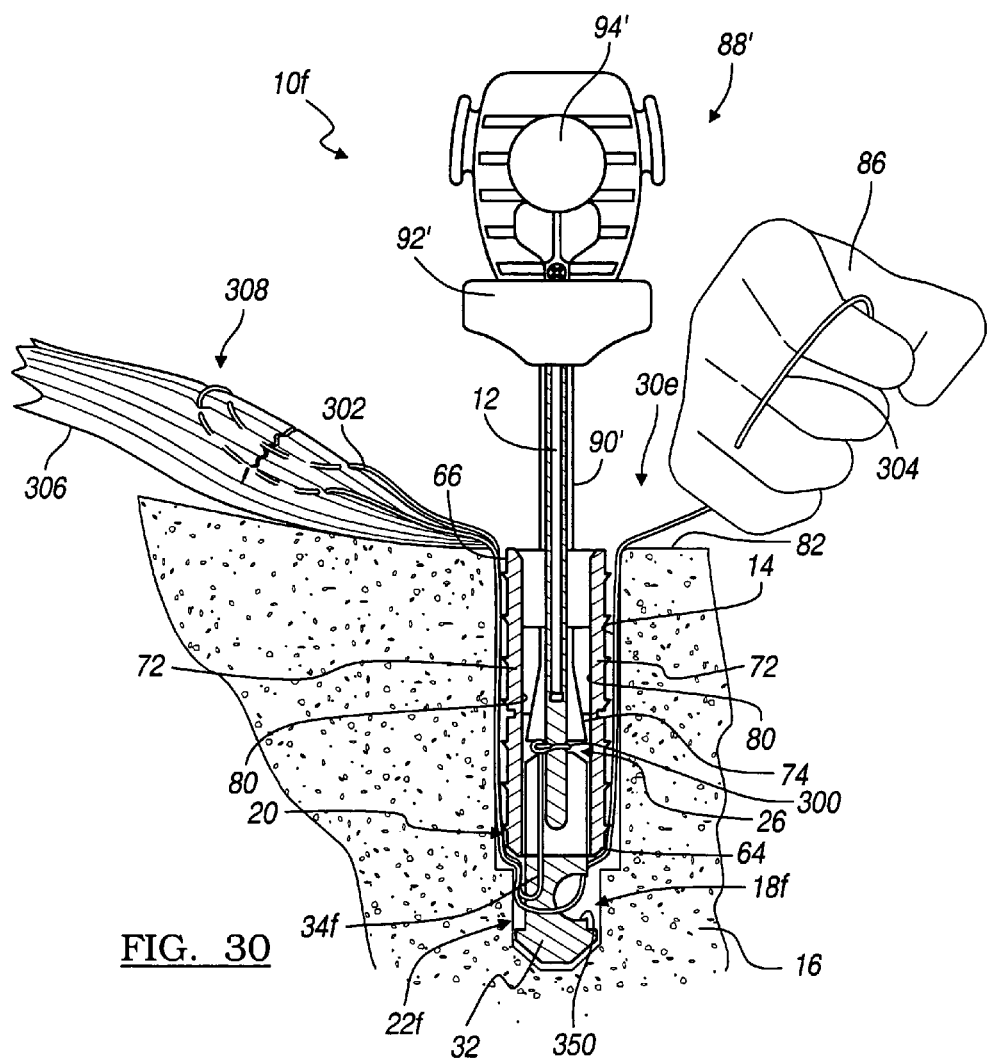
FIG. 30 is an environmental view of a second procedure associated with the suture anchor shown in FIG. 28.

With reference to FIG. 30, the suture anchor 10*f* can be inserted into the pre-drilled hole 14 formed in the boney structure 16. Next, as discussed herein, the hand 86 of the operator can be used to tighten the suture 30*e*, and thus the soft tissue 306, to the pre-drilled hole 14 by pulling the second end 304 of the suture 30*e* that extends from the pre-drilled hole 14. After the suture 30*e* is tightened, the expanding members 72 of the suture anchor 10*f* can be expanded to engage the pre-drilled hole 14 through the use of the actuator gun 56, syringe-type actuator 88 or syringe-type actuator 88', for example, as discussed previously with reference to FIGS. 4A and 4B, 4D and 9-12, respectively.

Figure 31:
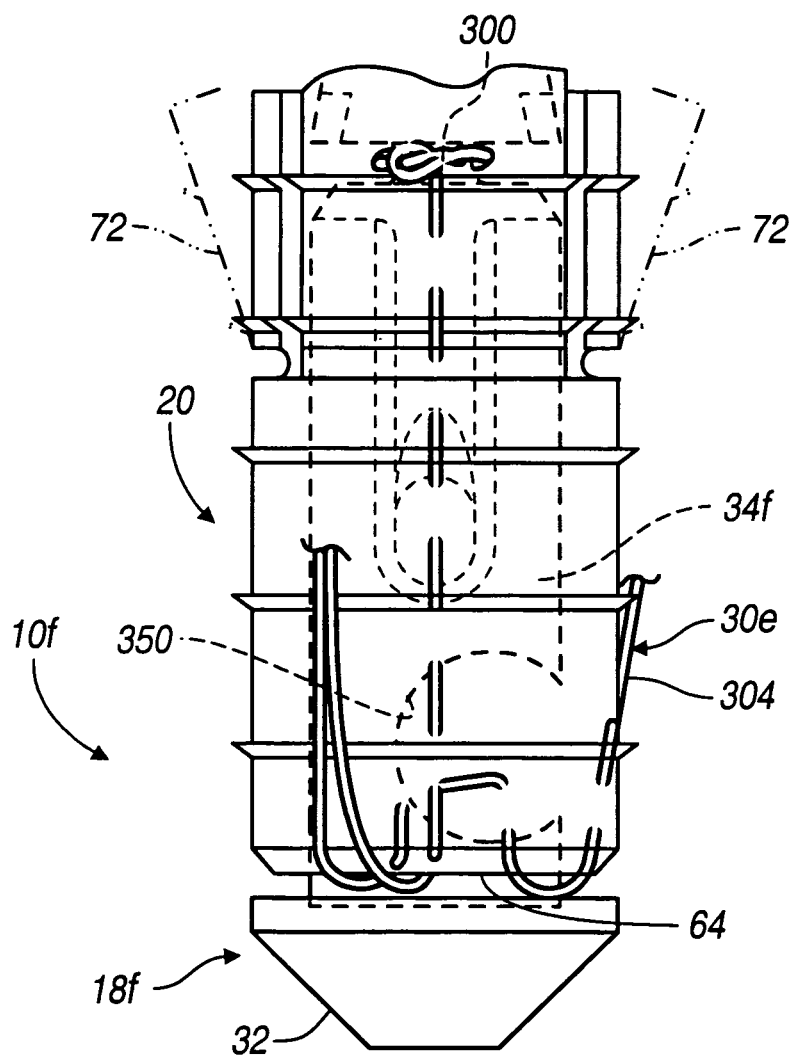
FIG. 31 is detailed front view of the suture anchor of FIG. 28 illustrating a suture fixed to the suture anchor.

When the suture anchor 10*f* is fully engaged to the pre-drilled hole 14, the tip 32 of the suture receiving portion 22*f* can be adjacent to the suture 30*e*, while the suture 30*e* is adjacent to the first end 64 of the sleeve 20, as best shown in FIG. 31. The compression of the suture 30*e* between the suture receiving portion 22*f* and the tip 32 can fix or lock the suture 30*e* to the suture anchor 10*f*. Thus, the suture anchor 10*f* can fix the second end 304 of the suture 30*e* to the suture anchor 10*f* without the use of a knot, while providing greater access for the operator to couple the second end 304 of the suture 30*e* to the sixth alternative insert 18*f* prior to the insertion of the suture anchor 10*f* into the pre-drilled hole 14. The portion of the second end 304 that extends from the pre-drilled hole 14 can then be trimmed if desired (not shown).

With reference to FIG. 32, a seventh alternative insert 18*g* is shown. The seventh alternative insert 18*g* can include a suture receiving portion 22*g*, the breakaway section 26, and the end section 24 for use with a suture anchor 10*g* substantially similar to the suture anchor 10*e* described with regard to FIGS. 21-27. As the breakaway section 26 and end section 24 of the seventh alternative insert 18*g* are substantially similar to the breakaway section 26 and end section 24 of the insert 18, the breakaway section 26 and end section 24 will not be discussed in detail with regard to the seventh alternative insert 18*g*. In addition, as the suture receiving portion 22*g* is substantially similar to the suture receiving portion 22*e* of the fifth alternative insert 18*e*, as discussed with FIGS. 21-27, only the modifications to the suture receiving portion 22*g* will be discussed herein.

As shown in FIG. 32, the suture receiving portion 22*g* can include a slot, for example, a C-shaped slot 360, which can be for receipt of the suture 30*e*. Generally, the slot 360 can be defined in a cylindrical body 34*g* of the seventh alternative insert 18*g*. As will be appreciated, the remainder of the cylindrical body 34*g* can be generally similar to the cylindrical body 34*e* that is illustrated in and described in conjunction with FIG. 21. The slot 360 can define a throughbore 362 and a necked portion 364. The necked portion 364 can define an aperture 366 for receipt of the first end 300 and second end 304 of the suture 30*e*. Generally, the necked portion 364 can be configured such that the first end 300 and second end 304 of the suture 30*e* can be hooked behind and retained by the necked portion 364.

As the assembly and deployment of the suture anchor 10*g* in the pre-drilled hole 14 is substantially similar to the deployment of the suture anchor 10*e* discussed with regard to FIGS. 21-27 and the suture anchor 10*f* discussed with regard to FIGS. 30 and 31, the assembly and deployment of the suture anchor 10*g* will not be discussed in detail herein. Briefly, however, the first end 300 of the suture 30*e* can be tied to the breakaway section 26 and the midsection 302 of the suture 30*e* can be coupled to the soft tissue 306 via the mattress stitch 308 or any other technique, such as a suture punch (not shown). Then, the hand 86 of the operator can thread or insert the second end 304 of the suture 30*e* into the slot 360 (not shown). Then, the suture anchor 10*g* can be inserted into the pre-drilled hole 14 and the hand 86 of the operator can be used to tighten the suture 30*e*, and thus the soft tissue 306, to the pre-drilled hole 14 by pulling the second end 304 of the suture 30*e* that extends from the pre-drilled hole 14 (not shown). This further removes any slack from the suture 30*e*. After the suture 30*e* is tightened, the expanding members 72 of the suture anchor 10*g* can be deployed to engage the pre-drilled hole 14.

When the suture anchor 10*g* is fully engaged to the pre-drilled hole 14, the tip 32 of the suture receiving portion 22*g* can be adjacent to the suture 30*e*, while the suture 30*e* is adjacent to the first end 64 of the sleeve 20, as best shown in FIG. 33. The compression of the suture 30*e* between the suture receiving portion 22*g* and the tip 32 can fix or lock the suture 30*e* to the suture anchor 10*g*. Thus, the suture anchor 10*g* can fix the second end 304 of the suture 30*e* to the suture anchor 10*g* without the use of a knot, while providing greater access for the operator to couple the second end 304 of the suture 30*e* to the seventh alternative insert 18*g* prior to the insertion of the suture anchor 10*g* into the pre-drilled hole 14. The portion of the second end 304 that extends from the pre-drilled hole 14 can then be trimmed if desired (not shown).

Figures 34, 35:
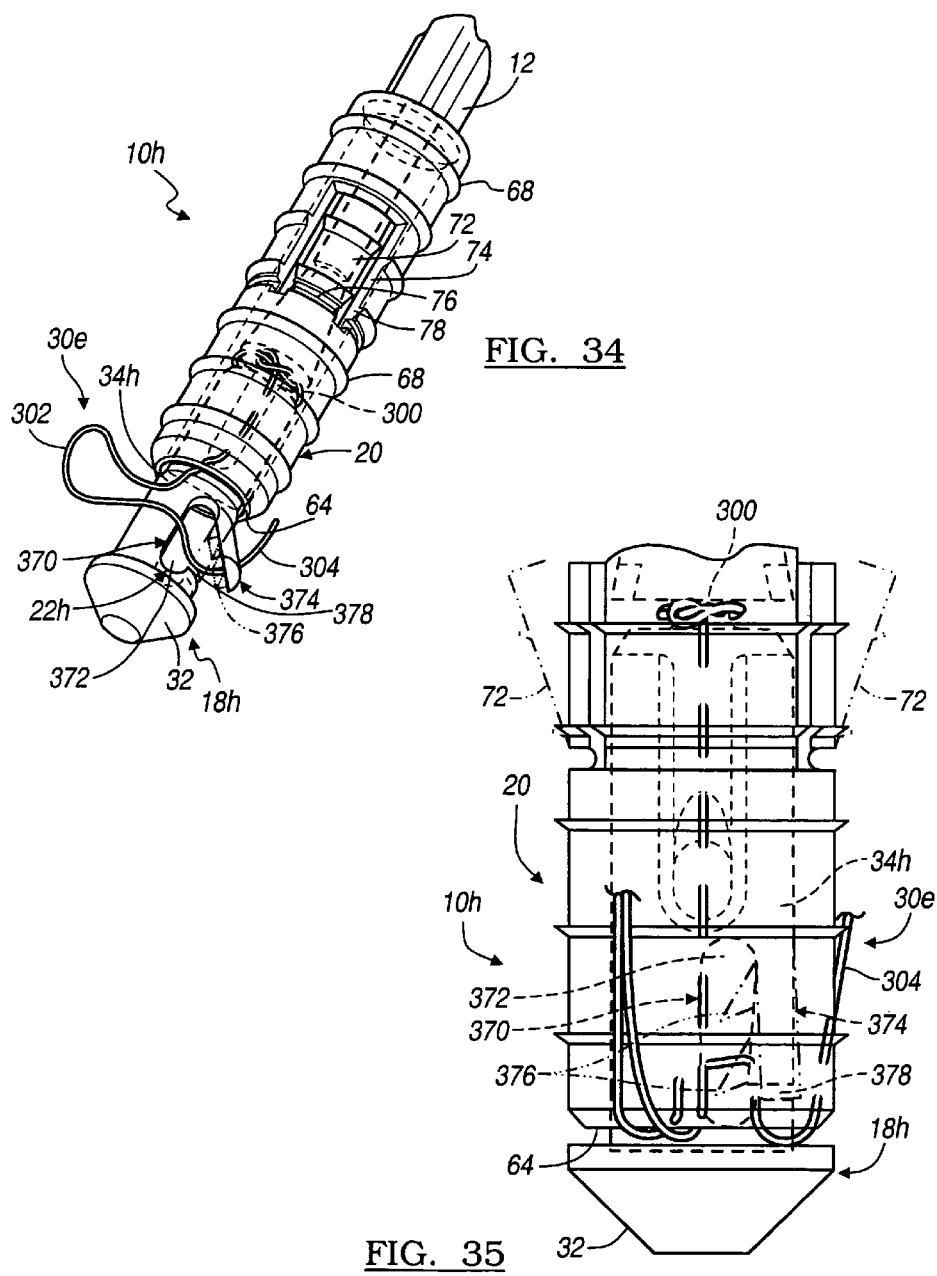
FIG. 34 is a perspective view of a eighth alternative expanding suture anchor having an actuator pin according to the present disclosure.
FIG. 35 is detailed front view of the suture anchor of FIG. 34 illustrating a suture fixed to the suture anchor.

With reference to FIG. 34, an eighth alternative insert 18*h* is shown. The eighth alternative insert 18*h* can include a suture receiving portion 22*h*, the breakaway section 26, and the end section 24 for use with a suture anchor 10*h* substantially similar to the suture anchor 10*e* described with regard to FIGS. 21-27. As the breakaway section 26 and end section 24 of the eighth alternative insert 18*h* are substantially similar to the breakaway section 26 and end section 24 of the insert 18, the breakaway section 26 and end section 24 will not be discussed in detail with regard to the eighth alternative insert 18*h*. In addition, as the suture receiving portion 22*h* is substantially similar to the suture receiving portion 22*e* of the fifth alternative insert 18*e*, as discussed with FIGS. 21-27, only the modifications to the suture receiving portion 22*h* will be discussed herein.

As shown in FIG. 34, the suture receiving portion 22*h* can include a hinged slot 370 which can be for receipt of the suture 30*e*. Generally, the hinged slot 370 can be defined in a cylindrical body 34*h* of the eighth alternative insert 18*h*. As will be appreciated, the remainder of the cylindrical body 34*h* can be generally similar to the cylindrical body 34*e* that is illustrated in and described in conjunction with FIG. 21.

The hinged slot 370 can define a throughbore 372 and can include a hinged portion 374. The hinged portion 374 can optionally include at least one or a plurality of barbs or projections 376. The throughbore 372 can be configured to retain the first end 300 and second end 304 of the suture 30*e*. The hinged portion 374 can be pivotably coupled to the cylindrical body 34*h* and can rotate from an opened position to a closed position. In the opened position, as shown in FIG. 34, the hinged portion 374 can define an aperture 378 for receipt of the first end 300 and second end 304 of the suture 30e to enable the suture 30e to enter the throughbore 372 of the hinged slot 370. In the closed position, the hinged portion 374 can substantially enclose the aperture 378 to retain the suture 30e within the throughbore 372, as shown in FIG. 35. Thus, generally, the hinged portion 374 can be sized such that in the closed position the hinged portion 374 can substantially enclose the aperture 378. The projections 376 are optional and can be coupled to or formed with the hinged portion 374 if desired. The projections 376 can extend into the throughbore 372 when the hinged portion 374 is in the closed position to further retain the suture 30e within the throughbore 372. The projections 376 are illustrated as triangular, however, any appropriate shape, such as annular or hooked, could be employed.

As the assembly and deployment of the suture anchor 10h in the pre-drilled hole 14 is substantially similar to the assembly and deployment of the suture anchor 10e discussed with regard to FIGS. 21-27 and the suture anchor 10f discussed with regard to FIGS. 30 and 31, the assembly and deployment of the suture anchor 10h will not be discussed in detail herein. Briefly, however, the first end 300 of the suture 30e can be tied to the breakaway section 26 and the midsection 302 of the suture 30e can be coupled to the soft tissue 306 via the mattress stitch 308 or any other technique, such as a suture punch (not shown). The hand 86 of the operator can thread or insert the second end 304 of the suture 30e into the hinged slot 370 (not shown). Then, the suture anchor 10h can be inserted into the pre-drilled hole 14 and the hand 86 of the operator can be used to tighten the suture 30e, and thus the soft tissue 306, to the pre-drilled hole 14 by pulling the second end 304 of the suture 30e that extends from the pre-drilled hole 14 (not shown). This further removes any slack from the suture 30e. After the suture 30e is tightened, the expanding members 72 of the suture anchor 10h can be deployed to engage the pre-drilled hole 14. During the deployment of the suture anchor 10h, as the eighth alternative insert 18h moves rearwardly in the sleeve 20, the hinged portion 374 can be pushed closed by the sleeve 20 to lock the suture 30e within the throughbore 372 of the suture receiving portion 22h.

When the suture anchor 10h is fully engaged to the pre-drilled hole 14, the tip 32 of the suture receiving portion 22h can be adjacent to the suture 30e, while the suture 30e is adjacent to the first end 64 of the sleeve 20, as best shown in FIG. 35. The compression of the suture 30e between the suture receiving portion 22h and the tip 32 can fix or lock the suture 30e to the suture anchor 10h. Thus, the suture anchor 10h can also fix the second end 304 of the suture 30e to the suture anchor 10h without the use of a knot. The portion of the second end 304 that extends from the pre-drilled hole 14 can then be trimmed if desired (not shown).

With reference to FIG. 36, a ninth alternative insert 18i is shown. The ninth alternative insert 18i can include a suture receiving portion 22i, the breakaway section 26, and the end section 24 for use with a suture anchor 10i substantially similar to the suture anchor 10 described with regard to FIGS. 1-7. As the breakaway section 26 and end section 24 of the ninth alternative insert 18i are substantially similar to the breakaway section 26 and end section 24 of the insert 18, the breakaway section 26 and end section 24 will not be discussed in detail with regard to the ninth alternative insert 18i. In addition, as the suture receiving portion 22i is substantially similar to the suture receiving portion 22 of the insert 18, as discussed with FIGS. 1-6B, only the modifications to the suture receiving portion 22i will be discussed herein.

As shown in FIG. 36, the suture receiving portion 22i includes the eyelet 36 and a hinged slot 400. Generally, the eyelet 36 and hinged slot 400 can each be defined in a cylindrical body 34i of the ninth alternative insert 18i. As will be appreciated, the remainder of the cylindrical body 34i can be generally similar to the cylindrical body 34 that is illustrated in and described in conjunction with FIGS. 1-6B. The eyelet 36 can be configured for receipt of the suture 30 therein, as discussed herein, while the hinged slot 400 can be configured for receipt of a suture 30i therein.

Figure 36A:
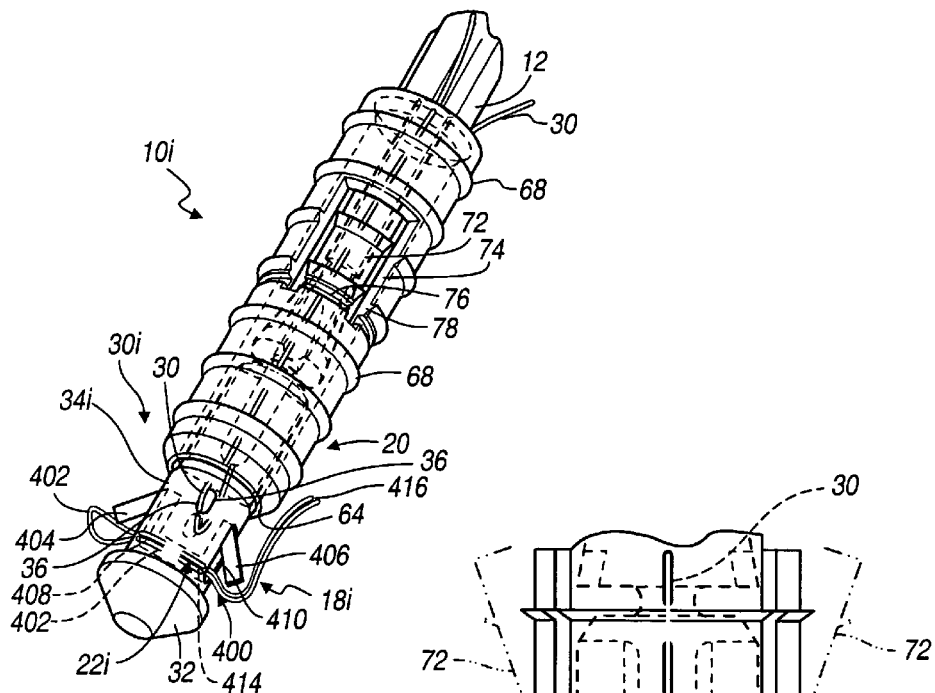
FIG. 36 is a perspective view of a ninth alternative expanding suture anchor having an actuator pin according to the present disclosure.
Figure 37B:
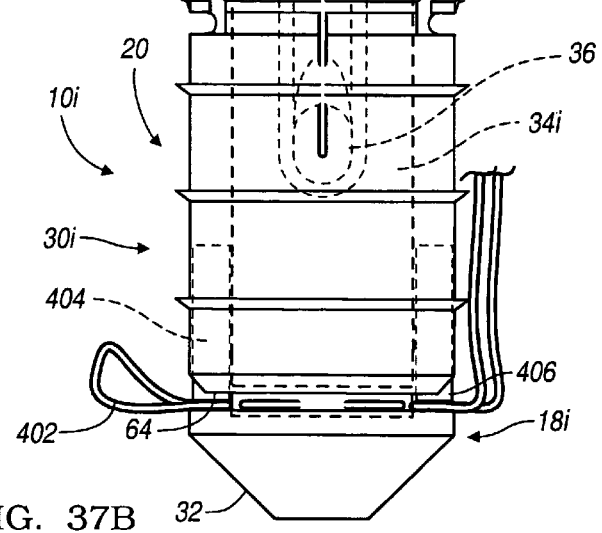
FIG. 37 is detailed front view of the suture anchor of FIG. 36 illustrating a suture fixed to the suture anchor.

The hinged slot 400 can include a throughbore 402, a first hinged portion 404 and a second hinged portion 406. The throughbore 402 defines a passageway for receipt of the suture 30i therethrough and can include a first end 408 and a second end 410. The first hinged portion 404 can be pivotably coupled to the first end 408 of the throughbore 402 and the second hinged portion 406 can be pivotably coupled to the second end 410 of the throughbore 402. The first hinged portion 404 and second hinged portion 406 can generally be pivotable from an opened position to a closed position. In the opened position, as shown in FIG. 36, the first hinged portion 404 and second hinged portion 406 can enable the suture 30i to be received into and through the throughbore 402. In the closed position, as shown in FIG. 37, the first hinged portion 404 and second hinged portion 406 can generally pivot to enclose the first end 408 and second end 410 of the throughbore 402, respectively, to secure or lock the suture 30i within the throughbore 402. Thus, generally, the first hinged portion 404 and the second hinged portion 406 can be sized to create an interference fit between the suture 30i, the first and second hinged portion 404, 406 and the throughbore 402 to lock the suture 30i to the ninth alternative insert 18i.

The suture 30i can include a first end 412, a midsection 414 and a second end 416. The suture 30i can be used to couple multiple suture anchors 10 together, wherein the reference numeral "10" denotes all of the suture anchors 10. Generally, the first end 412 of the suture 30i can be coupled to an adjacent suture anchor 10 (not specifically shown) and the midsection 414 of the suture 30i can pass through the throughbore 402 to secure the suture 30i to the suture anchor 10i. The second end 416 of the suture 30i can then be coupled to another suture anchor 10, or can be trimmed. Alternatively, the midsection 414 of the suture 30i can be coupled to additional soft tissue (not shown). If the midsection 414 is coupled to additional soft tissue, then the first end 412 and second end 416 of the suture 30i can pass through the throughbore 402 to couple the additional soft tissue to the suture anchor 10, as shown in FIG. 36A.

As the assembly and deployment of the suture anchor 10i in the pre-drilled hole 14 is substantially similar to the deployment of the suture anchor 10 discussed with regard to FIGS. 4A-6B and the suture anchor 10a discussed with regard to FIGS. 8-12, the assembly and deployment of the suture anchor 10i will not be discussed in detail herein. Briefly, however, in order to employ the suture anchor 10i, the suture 30 can be threaded through the eyelet 36 of the ninth alternative insert 18i and then the sleeve 20 can be disposed over the ninth alternative insert 18i (not specifically shown). The suture 30i can then be coupled to an adjacent suture anchor 10 or to the additional soft tissue via a mattress stitch or any other technique, such as a suture punch (not shown). If the suture 30i is coupled to an adjacent suture anchor 10, then the hand 86 of the operator can thread or insert the second end 416 of the suture 30e into the throughbore 402 until the midsection 414 is received in the throughbore 402 of hinged slot 400, and the second end 416 of the suture 30i extends beyond the second end 410 of the throughbore 402. If the suture 30i is coupled to the additional soft tissue, then the hand 86 of the operator can thread or insert the first end 412 and the second end 416 of the suture 30i into the hinged slot 400 (not shown). Once the suture 30i is threaded through the hinged slot 400, the suture anchor 10i can be inserted into the pre-drilled hole 14.

The hand 86 of the operator can be used to tighten the suture 30i to the pre-drilled hole 14 by pulling the respective first end 414 and/or second end 416 of the suture 30i that extends from the pre-drilled hole 14. This further removes any slack from the suture 30i (not shown). After the suture 30i is tightened, the expanding members 72 of the suture anchor 10i can be deployed to engage the pre-drilled hole 14. During the deployment of the suture anchor 10i, as the ninth alternative insert 18i moves rearwardly in the sleeve 20, the first hinged portion 404 and second hinged portion 406 can be pushed closed by the sleeve 20 to lock the suture 30i within the throughbore 402 of the suture receiving portion 22i as shown in FIGS. 37 and 37A. In addition, if necessary, the suture 30 coupled to the eyelet 36 can be pulled by the hand 86 of the operator to fully expand the expanding members 72 in soft boney tissue, as discussed herein.

When the suture anchor 10i is fully engaged to the pre-drilled hole 14, the tip 32 of the suture receiving portion 22i can be adjacent to the suture 30i, while the suture 30i is adjacent to the first end 64 of the sleeve 20, as best shown in FIGS. 37 and 37A. The compression of the suture 30i between the suture receiving portion 22i and the tip 32 can fix or lock the suture 30i to the suture anchor 10i. Thus, the suture anchor 10i can fix the first end 412 (FIG. 37), and the first end 412 and the second end 416 (FIG. 37A) of the suture 30i to the suture anchor 10i without the use of a knot. The portion of the first end 412 and/or second end 416 that extends from the pre-drilled hole 14 can then be trimmed if desired (not shown).

Figures 38, 39:
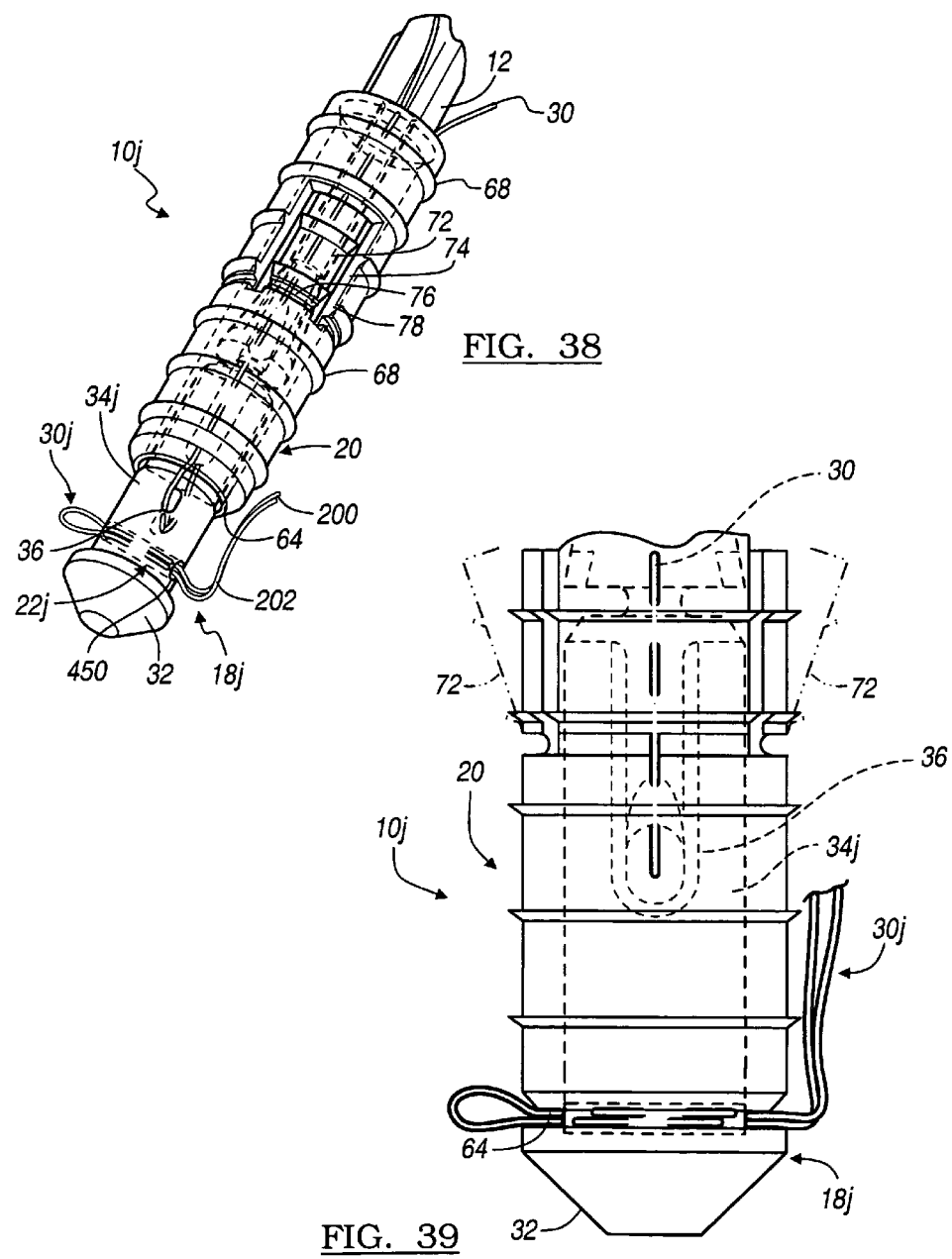
FIG. 38 is a perspective view of a tenth alternative expanding suture anchor having an actuator pin according to the present disclosure.
FIG. 39 is detailed front view of the suture anchor of FIG. 38 illustrating a suture fixed to the suture anchor.

With reference to FIG. 38, a tenth alternative insert 18j is shown. The tenth alternative insert 18j can include a suture receiving portion 22j, the breakaway section 26, and the end section 24 for use with a suture anchor 10j substantially similar to the suture anchor 10 described with regard to FIGS. 1-6B. As the breakaway section 26 and end section 24 of the tenth alternative insert 18j are substantially similar to the breakaway section 26 and end section 24 of the insert 18, the breakaway section 26 and end section 24 will not be discussed in detail with regard to the tenth alternative insert 18j. In addition, as the suture receiving portion 22j is substantially similar to the suture receiving portion 22 of the insert 18, as discussed with FIGS. 1-6B, only the modifications to the suture receiving portion 22j will be discussed herein.

As shown in FIG. 36, the suture receiving portion 22j includes the eyelet 36 and a second formed eyelet 450. Generally, the eyelet 36 and second formed eyelet 450 can each be defined in a cylindrical body 34j of the tenth alternative insert 18j. As will be appreciated, the remainder of the cylindrical body 34j can be generally similar to the cylindrical body 34 that is illustrated in and described in conjunction with FIGS. 1-6B. The eyelet 36 can be configured for receipt of the suture 30 therein, as discussed previously, while the second formed eyelet 450 can be configured for receipt of the suture 30j therein.

The second formed eyelet 450 can generally be formed perpendicular to the eyelet 36; however, the second formed eyelet 450 could be formed in any appropriate orientation with regard to the eyelet 36, such as parallel. The second formed eyelet 450 defines a passageway for receipt of a suture 30j therethrough. The suture 30j can be used to couple multiple suture anchors 10 together, wherein the reference numeral "10" denotes all of the suture anchors 10, or the suture 30j can be used to couple additional soft tissue to the suture anchor 10j. The suture 30j can include a first end 418, a midsection 420 and a second end 422. The midsection 420 can be coupled to either the suture anchor 10 or additional soft tissue, while the first end 418 and second end 422 can pass through the second formed eyelet 450 to couple the suture 30j to the suture anchor 10j.

As the assembly and deployment of the suture anchor 10j in the pre-drilled hole 14 is substantially similar to the assembly and deployment of the suture anchor 10 discussed with regard to FIGS. 4A-6B and the suture anchor 10a discussed with regard to FIGS. 8-12, the assembly and deployment of the suture anchor 10j will not be discussed in detail herein. Briefly, however, in order to employ the suture anchor 10j, the suture 30 can be threaded through the eyelet 36 of the tenth alternative insert 18j and then the sleeve 20 can be disposed over the tenth alternative insert 18j (not specifically shown). The suture 30j can then be coupled to an adjacent suture anchor 10 or to additional soft tissue via the mattress stitch or any other technique, such as a suture punch (not shown).

If the suture 30j is coupled to an adjacent suture anchor 10, then the hand 86 of the operator can thread or insert the second end 416 of the suture 30j into the second formed eyelet 450 until the midsection 414 is received in the second formed eyelet 450, and the second end 416 of the suture 30j extends beyond the suture anchor 10j. If the suture 30i is coupled to the additional soft tissue, then the hand 86 of the operator can thread or insert the first end 412 and the second end 416 of the suture 30j into the second formed eyelet 450 (not shown). Once the suture 30j is threaded through the second formed eyelet 450, the suture anchor 10j can be inserted into the pre-drilled hole 14.

As discussed herein, the hand 86 of the operator can be used to tighten the suture 30j to the pre-drilled hole 14 by pulling the first end 418 and second end 416 of the suture 30j that extends from the pre-drilled hole 14 (not shown). After the suture 30j is tightened, the expanding members 72 of the suture anchor 10j can be deployed to engage the pre-drilled hole 14. It should be noted, however, that if necessary, the suture 30 coupled to the eyelet 36 can be pulled by a hand 86 of an operator to fully expand the expanding members 72, as discussed herein.

When the suture anchor 10j is fully engaged to the pre-drilled hole 14, the tip 32 of the suture receiving portion 22j can be adjacent to the suture 30j, while the suture 30j is adjacent to the first end 64 of the sleeve 20, as best shown in FIG. 39. The compression of the suture 30j between the suture receiving portion 22j and the tip 32 can fix or lock the suture 30j to the suture anchor 10j. Thus, the suture anchor 10j can fix the first end 412 and second end 416 of the suture 30j to the suture anchor 10j without the use of a knot. The portion of the first end 412 and second end 416 of the suture 30j that extends from the pre-drilled hole 14 can then be trimmed if desired (not shown).

Figures 40, 41:
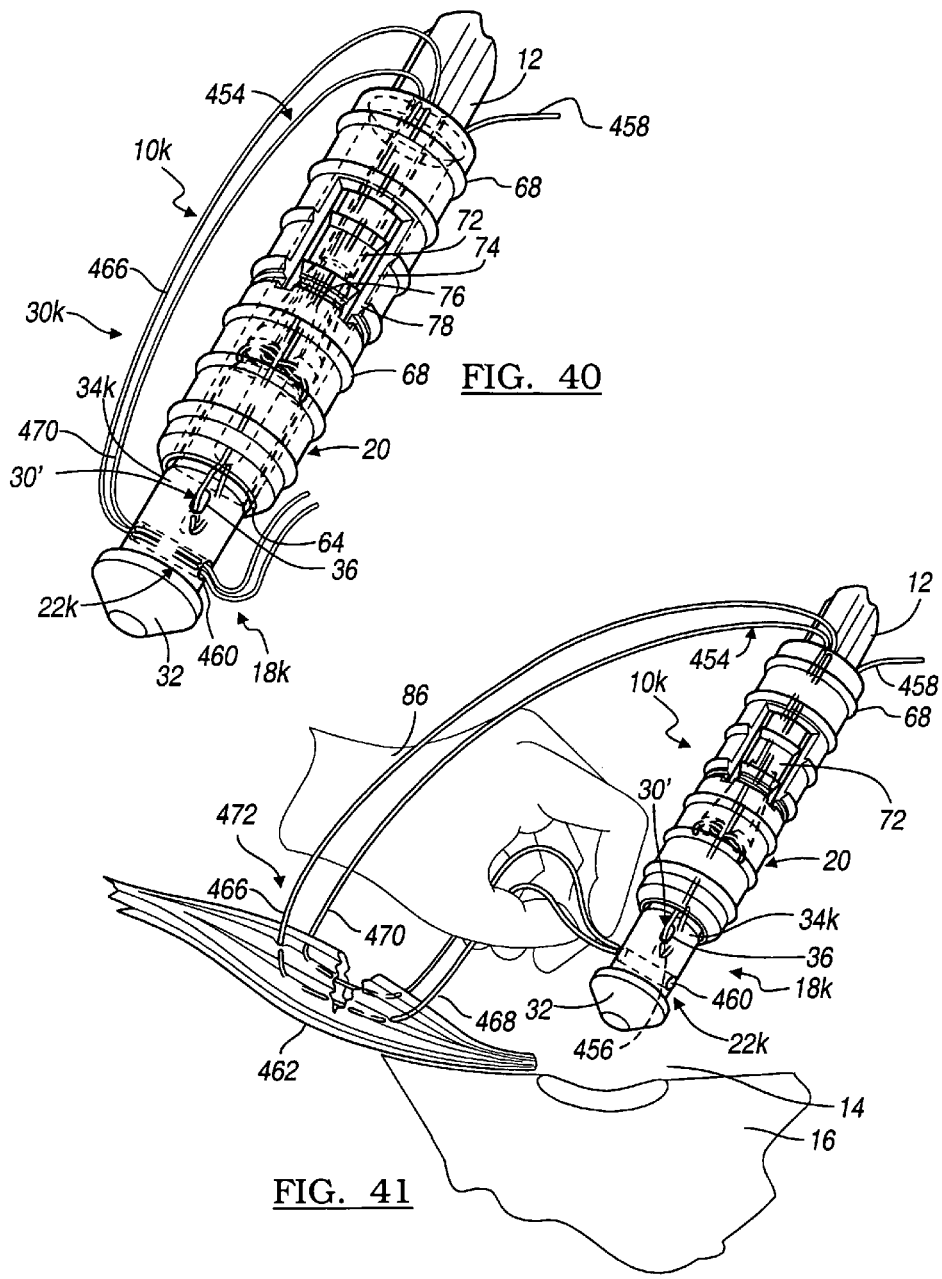
FIG. 40 is a perspective view of a eleventh alternative expanding suture anchor having an actuator pin according to the present disclosure.
FIG. 41 is an environmental view of a procedure associated with the suture anchor shown in FIG. 40.

With reference to FIG. 40, an eleventh alternative insert 18k is shown. The eleventh alternative insert 18k can include a suture receiving portion 22k, the breakaway section 26, and the end section 24 for use with a suture anchor 10k substantially similar to the suture anchor 10e described with regard to FIGS. 21-27. As the breakaway section 26 and end section 24 of the eleventh alternative insert 18k are substantially similar to the breakaway section 26 and end section 24 of the insert 18, the breakaway section 26 and end section 24 will not be discussed in detail with regard to the eleventh alternative insert 18k. In addition, as the suture receiving portion 22k is substantially similar to the suture receiving portion 22e of the fifth alternative insert 18e, as discussed with FIGS. 21-27, only the modifications to the suture receiving portion 22k will be discussed herein.

As shown in FIG. 40, the suture receiving portion 22k can include the eyelet 36 and a second formed eyelet 460. Generally, the eyelet 36 and second formed eyelet 460 can each be defined in a cylindrical body 34k of the eleventh alternative insert 18k. As will be appreciated, the remainder of the cylindrical body 34k can be generally similar to the cylindrical body 34 that is illustrated in and described in conjunction with FIGS. 1-6B. The eyelet 36 can be configured for receipt of a suture 30' therein, while the second formed eyelet 460 can be configured for receipt of the suture 30k therein. The suture 30' can include a first end 454, a midsection 456 and second end 458. The first end 454 of the suture 30' can be coupled to a suture anchor 10 or additional soft tissue 462 and can pass through the second formed eyelet 460 to couple the suture 30' to the suture anchor 10k. The midsection 456 can be received through the eyelet 36 to further retain the suture 30' within the suture anchor 10k. The second end 458 can extend from the second end 66 of the sleeve 20.

The second formed eyelet 460 can generally be formed perpendicular to the eyelet 36; however, the second formed eyelet 460 could be formed in any appropriate orientation with regard to the eyelet 36, such as parallel. The second formed eyelet 460 defines a passageway for receipt of the suture 30k therethrough. The suture 30k can be used to couple multiple suture anchors 10 together, wherein the reference numeral "10" denotes all of the suture anchors 10, or the suture 30k can be used to couple additional soft tissue 462 to the suture anchor 10k. The suture 30k can include a first end 464, a midsection 466, and a second end 468. The first end 464 can be coupled to the breakaway section 26 of the eleventh alternative insert 18k. The midsection 466 can be coupled to either the suture anchor 10 or to the additional soft tissue 462. The second end 468 of the suture 30k can pass through the second formed eyelet 460 to couple the suture 30k to the suture anchor 10k.

Typically, in order to employ the suture anchor 10k, with additional reference to FIG. 41, the suture 30' can be threaded through the eyelet 36 of the eleventh alternative insert 18k and then the first end 412 of the suture 30k can be tied to the breakaway section 26. The sleeve 20 can be disposed over the eleventh alternative insert 18k such that the suture 30' and the suture 30k extend from the second end 66 of the sleeve 20. Then, the midsection 466 of the suture 30k and a portion 470 of the first end 454 of the suture 30' can then be coupled to an adjacent suture anchor 10 (not shown) or to the additional soft tissue 462 via the mattress stitch 472 or any other technique, such as a suture punch. If the suture 30' and the suture 30k are coupled to an adjacent suture anchor 10, then the hand 86 of the operator can thread or insert the first end 454 of the suture 30' and the second end 468 of the suture 30k into the second formed eyelet 460 until the first end 454 of the suture 30' and the second end 468 of the suture 30k extend beyond the suture anchor 10k (not shown).

If the midsection 466 of the suture 30k and the portion 470 of the first end 454 of the suture 30' are coupled to the additional soft tissue 462, then the hand 86 of the operator can thread or insert the first end 454 of the suture 30' and the second end 468 of the suture 30k into the second formed eyelet 460, as shown in FIG. 41. Once the first end 454 of the suture 30' and the suture 30k are threaded through the second formed eyelet 460, the suture anchor 10k can be inserted into the pre-drilled hole 14.

The hand 86 of the operator can be used to tighten the additional soft tissue 462 to the pre-drilled hole 14 by pulling the suture 30k and the first end 454 of the suture 30' that extends from the pre-drilled hole 14. After the suture 30' and suture 30k are tightened, the expanding members 72 of the suture anchor 10k can be deployed to engage the pre-drilled hole 14. As the deployment of the suture anchor 10k in the pre-drilled hole 14 is substantially similar to the deployment of the suture anchor 10 discussed with regard to FIGS. 4A-6B and the suture anchor 10e discussed with regard to FIGS. 21-27, the deployment of the suture anchor 10k will not be discussed in detail herein. It should be noted, however, that if necessary, the first end 454 and second end 458 of the suture 30' coupled to the eyelet 36 can be pulled by the hand 86 of the operator to fully expand the expanding members 72 in the case of soft boney tissue, as discussed herein.

Figure 42:
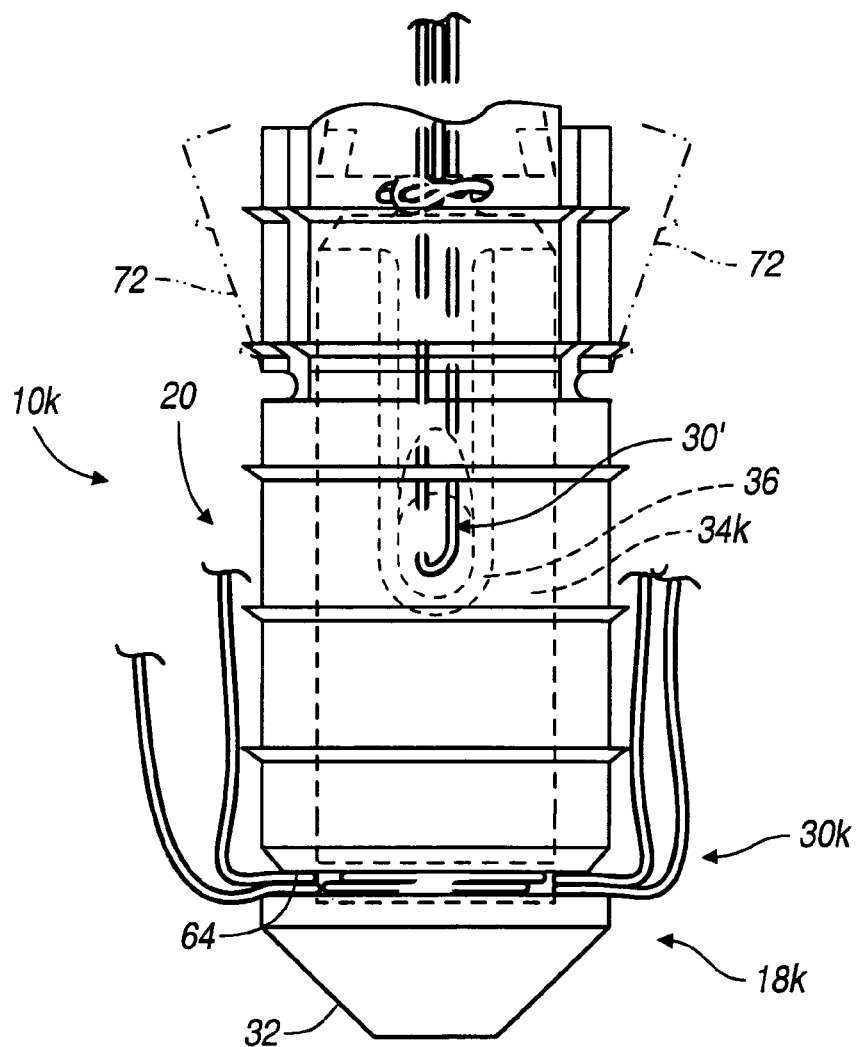
FIG. 42 is detailed front view of the suture anchor of FIG. 40 illustrating a suture fixed to the suture anchor.

When the suture anchor 10k is fully engaged to the pre-drilled hole 14, the tip 32 of the suture receiving portion 22k can be adjacent to the suture 30' and the suture 30k, while the suture 30' and suture 30k are adjacent to the first end 64 of the sleeve 20, as best shown in FIG. 42. The compression of the suture 30' and the suture 30k between the suture receiving portion 22k and the tip 32 can fix or lock the suture 30' and the suture 30k to the suture anchor 10k. Thus, the suture anchor 10k can fix the suture 30' and the suture 30k to the suture anchor 10k without the use of a knot. The portion of the second end 458 of the suture 30' and the suture 30k that extend from the pre-drilled hole 14 can then be trimmed if desired (not shown).

The description of these teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A method for attaching a soft tissue to a boney structure comprising:
    forming a cavity in a boney structure;
    passing a suture having first and second ends through a soft tissue;
    passing the first and second ends of the suture into a suture-receiving opening of an insert of a suture anchor;
    inserting the suture anchor into the cavity;
    applying a retractive force on the insert through a sleeve of the suture anchor;
    pivoting an expanding element of the sleeve with the insert, the expanding element defined by a U-shaped slot formed in a midsection of the sleeve so as to be spaced apart from a proximal end and a distal end of the sleeve and surrounded by the sleeve, the U-shaped slot defining three sides of a periphery of the expanding element, with a fourth side of the periphery of the expanding element hingeably coupled to the midsection of the sleeve; and
    anchoring first and second portions of the suture in contact with a wall of the cavity and the sleeve of the suture anchor without a knot.

2. The method of claim 1, wherein applying a retractive force includes applying a retractive force to an actuator pin, the actuator pin molded to the insert at a breakaway portion of the insert.

3. The method of claim 2, further comprising removing the actuator pin by breaking off the breakaway portion of the insert.

4. The method of claim 1, wherein passing the first and second ends of the suture through a suture-receiving opening of an insert comprises passing the first and second ends of the suture through a hole extending transversely through a cylindrical body of the insert.

5. The method of claim 1, wherein passing the first and second ends of the suture into a suture-receiving opening of an insert of a suture anchor includes passing the first and second ends of the suture through a C-shaped opening extending through a cylindrical body of the insert.

6. The method of claim 5, wherein passing the first and second ends of the suture through a C-shaped opening includes:
opening a hinged portion of the C-shaped opening;
passing the first and second ends of the suture through a bore of the C-shaped opening; and
closing the hinged portion of the C-shaped opening.

7. The method of claim 6, further comprising retaining the suture in the bore by pivoting the hinged portion to close the bore.

8. The method of claim 1, wherein passing the first and second ends of the suture into a suture-receiving opening of an insert of a suture anchor includes:
opening first and second hinged portions attached to first and second ends of a bore of the opening;
passing the first and second ends of the suture through the bore; and
closing the first and second hinged portions.

9. The method of claim 1, wherein the sleeve includes external ridges.

10. The method of claim 1, further comprising:
passing a second suture through a through bore of the insert, the through bore not intersecting the opening of the insert; and
coupling the second suture to a second suture anchor.

11. The method of claim 1, wherein pivoting an expanding element of the sleeve includes pivoting first and second opposed expanding elements at a midsection of the sleeve.

12. A method for attaching a soft tissue to a boney structure comprising:
forming a cavity in a boney structure;
passing a suture having first and second ends through a soft tissue;
opening first and second hinged portions attached to first and second open ends of a through bore of an insert of the suture anchor;
passing the first and second ends of the suture into the through bore;
closing the first and second hinged portions;
inserting the suture anchor into the cavity;
applying a retractive force on the insert through a sleeve of the suture anchor;
pivoting an expanding element of the sleeve with the insert, the expanding element defined by a U-shaped slot formed in a midsection of the sleeve so as to be spaced apart from a proximal end and a distal end of the sleeve and surrounded by the sleeve, the U-shaped slot defining three sides of a periphery of the expanding element, with a fourth side of the periphery of the expanding element hingeably coupled to the midsection of the sleeve;
retaining the suture in the through bore by pivoting the first and second hinged portions to close the through bore; and
anchoring first and second portions of the suture in contact with a wall of the cavity and the sleeve of the suture anchor without a knot.

13. A method for attaching a soft tissue to a boney structure comprising:
forming a cavity in a boney structure;
passing a suture having first and second ends through a soft tissue;
passing a first end of the suture transversely into a C-shaped slot of an insert of a suture anchor, the C-shaped slot having a first through bore and a necked portion;
coupling the second end of the suture directly to a breakaway portion of the insert;
inserting the suture anchor into the cavity;
applying a retractive force on the insert through a sleeve of the suture anchor;
pivoting an expanding element hingedly coupled at a midsection of the sleeve;
expanding the sleeve; and
anchoring first and second portions of the suture in contact with a wall of the cavity and the sleeve of the suture anchor.

14. The method of claim 13, wherein applying a retractive force includes applying a retractive force to an actuator pin, the actuator pin molded to the insert at the breakaway portion of the insert.

15. The method of claim 14, further comprising removing the actuator pin by breaking off the breakaway portion of the insert.

16. The method of claim 13, further comprising retaining the suture in the through bore by pivoting a hinged portion coupled to the through bore to close the through bore.

17. The method of claim 13, wherein the through bore has first and second open ends, a first hinged portion pivotably coupled to the first end and a second hinged portion pivotable coupled to the second end.

18. The method of claim 13, further comprising:
passing a second suture through a second through bore of the insert; and
coupling the second suture to a second suture anchor.

19. The method of claim 13, wherein the second end of the suture is knotted directly to the breakaway portion of the insert.

20. A method for attaching a soft tissue to a boney structure comprising:
forming a cavity in a boney structure;
passing a first suture having first and second ends through a soft tissue;
passing a first end of the first suture through a first through bore of an insert of a suture anchor;
coupling the second end of the first suture directly to a breakaway portion of the insert;
passing a second suture through a second through bore of the insert, the second through bore not communicating with the first through bore;
inserting the suture anchor into the cavity;
applying a retractive force on the insert through a sleeve of the suture anchor;
expanding the sleeve;
coupling the second suture to a second suture anchor; and
anchoring first and second portions of the first suture in contact with a wall of the cavity and the sleeve of the suture anchor.

21. The method of claim 20, further comprising attaching the second suture to soft tissue.

22. The method of claim 20, wherein the first through bore is substantially orthogonal to the second through bore.

23. The method of claim 20, wherein the sleeve includes external ridges.

24. The method of claim 20, wherein the second end of the first suture is knotted directly to the breakaway portion of the insert.

* * * * *